US009615766B2

(12) United States Patent
Gaw

(10) Patent No.: US 9,615,766 B2
(45) Date of Patent: Apr. 11, 2017

(54) IMPEDANCE MEASUREMENT PROCESS

(75) Inventor: Richelle Leanne Gaw, Greenslopes (AU)

(73) Assignee: IMPEDIMED LIMITED, Queensland (AU)

( * ) Notice: Subject to any disclaimer, the term of this patent is extended or adjusted under 35 U.S.C. 154(b) by 977 days.

(21) Appl. No.: 13/131,859

(22) PCT Filed: Nov. 27, 2009

(86) PCT No.: PCT/AU2009/001553
§ 371 (c)(1),
(2), (4) Date: Jul. 26, 2011

(87) PCT Pub. No.: WO2010/060152
PCT Pub. Date: Jun. 3, 2010

(65) Prior Publication Data
US 2011/0313311 A1    Dec. 22, 2011

(30) Foreign Application Priority Data

Nov. 28, 2008  (AU) ................. 2008906169

(51) Int. Cl.
*A61B 5/05* (2006.01)
*A61B 5/053* (2006.01)
(Continued)

(52) U.S. Cl.
CPC ............ *A61B 5/053* (2013.01); *A61B 5/0531* (2013.01); *A61B 5/0536* (2013.01);
(Continued)

(58) Field of Classification Search
CPC ...... A61B 5/0537; A61B 5/053; A61B 5/4872
(Continued)

(56) References Cited

U.S. PATENT DOCUMENTS 3,316,896 A    5/1967  Thomasset
3,834,374 A    9/1974  Ensanian et al.
(Continued)

FOREIGN PATENT DOCUMENTS

CA    2231038 A1    11/1999
CA    2613524 A1    1/2007
(Continued)

OTHER PUBLICATIONS

Forslund et al., Evaluation of modified multicompartment models to calculate body composition in healthy males, Am. J. of Clin. Nutrition, 1996; 63: 856-62.
(Continued)

*Primary Examiner* — Daniel Cerioni
(74) *Attorney, Agent, or Firm* — Hahn & Associates PLLC; Roger C. Hahn

(57) ABSTRACT

Apparatus for use in performing impedance measurements on a subject, the apparatus including a probe having a plurality of electrodes, the probe being configured to allow at least some of the electrodes to be in contact with at least part of the subject and a processing system for, determining at least one first impedance value, measured at a site using a first electrode configuration, determining at least one second impedance value, measured at the site using a second electrode configuration and determining an indicator indicative of the presence, absence or degree of an anomaly using the first and second impedance values.

18 Claims, 24 Drawing Sheets

(51) Int. Cl.
*A61B 5/145* (2006.01)
*A61B 5/00* (2006.01)

(52) U.S. Cl.
CPC ........ *A61B 5/0538* (2013.01); *A61B 5/14535* (2013.01); *A61B 5/4331* (2013.01); *A61B 5/4337* (2013.01); *A61B 2562/0209* (2013.01); *A61B 2562/066* (2013.01)

(58) Field of Classification Search
USPC .......................................................... 600/547
See application file for complete search history.

(56) References Cited

U.S. PATENT DOCUMENTS

| | | | |
|---|---|---|---|
| 3,851,641 A | 12/1974 | Toole et al. | |
| 3,871,359 A | 3/1975 | Pacela | |
| 4,008,712 A | 2/1977 | Nyboer | |
| 4,034,854 A | 7/1977 | Bevilacqua | |
| 4,144,878 A | 3/1979 | Wheeler | |
| RE30,101 E | 9/1979 | Kubicek et al. | |
| 4,184,486 A | 1/1980 | Papa | |
| 4,291,708 A | 9/1981 | Frei et al. | |
| 4,314,563 A | 2/1982 | Wheeler | |
| 4,353,372 A | 10/1982 | Ayer | |
| 4,365,634 A | 12/1982 | Bare et al. | |
| 4,401,356 A | 8/1983 | Bare | |
| 4,407,288 A | 10/1983 | Langer et al. | |
| 4,407,300 A | 10/1983 | Davis | |
| 4,450,527 A | 5/1984 | Sramek | |
| 4,458,694 A | 7/1984 | Sollish et al. | |
| 4,486,835 A | 12/1984 | Bai et al. | |
| 4,537,203 A | 8/1985 | Machida | |
| 4,539,640 A | 9/1985 | Fry et al. | |
| 4,557,271 A | 12/1985 | Stoller et al. | |
| 4,583,549 A | 4/1986 | Manoli | |
| 4,602,338 A | 7/1986 | Cook | |
| 4,617,939 A | 10/1986 | Brown et al. | |
| 4,638,807 A | 1/1987 | Ryder | |
| 4,646,754 A | 3/1987 | Seale | |
| 4,686,477 A | 8/1987 | Givens et al. | |
| 4,688,580 A | 8/1987 | Ko et al. | |
| 4,695,955 A | 9/1987 | Faisandier | |
| 4,763,660 A | 8/1988 | Kroll et al. | |
| 4,793,362 A | 12/1988 | Tedner | |
| 4,832,608 A | 5/1989 | Kroll | |
| 4,890,630 A | 1/1990 | Kroll et al. | |
| 4,895,163 A | 1/1990 | Libke et al. | |
| 4,905,705 A | 3/1990 | Kizakevich et al. | |
| 4,911,175 A | 3/1990 | Shizgal | |
| 4,924,875 A | 5/1990 | Chamoun | |
| 4,942,880 A | 7/1990 | Slovak | |
| 4,951,682 A | 8/1990 | Petre | |
| 5,025,784 A | 6/1991 | Shao et al. | |
| 5,063,937 A | 11/1991 | Ezenwa et al. | |
| 5,078,134 A | 1/1992 | Heilman et al. | |
| 5,086,781 A | 2/1992 | Bookspan | |
| 5,101,828 A | 4/1992 | Welkowitz et al. | |
| 5,143,079 A | 9/1992 | Frei et al. | |
| 5,197,479 A | 3/1993 | Hubelbank et al. | |
| 5,199,432 A | 4/1993 | Quedens et al. | |
| 5,246,008 A | 9/1993 | Mueller | |
| 5,280,429 A | 1/1994 | Withers | |
| 5,305,192 A | 4/1994 | Bonte et al. | |
| 5,309,917 A | 5/1994 | Wang et al. | |
| 5,311,878 A | 5/1994 | Brown et al. | |
| 5,372,141 A | 12/1994 | Gallup et al. | |
| 5,415,164 A | 5/1995 | Faupel et al. | |
| 5,421,344 A | 6/1995 | Popp | |
| 5,423,326 A | 6/1995 | Wang et al. | |
| 5,449,000 A | 9/1995 | Libke et al. | |
| 5,454,377 A | 10/1995 | Dzwonczyk et al. | |
| 5,465,730 A | 11/1995 | Zadehkoochak et al. | |
| 5,469,859 A | 11/1995 | Tsoglin et al. | |
| 5,503,157 A | 4/1996 | Sramek | |
| 5,505,209 A | 4/1996 | Reining | |
| 5,511,553 A | 4/1996 | Segalowitz | |
| 5,526,808 A | 6/1996 | Kaminsky | |
| 5,529,072 A | 6/1996 | Sramek | |
| 5,544,662 A | 8/1996 | Saulnier et al. | |
| 5,557,242 A | 9/1996 | Wetherell | |
| 5,562,607 A | 10/1996 | Gyory | |
| 5,588,429 A | 12/1996 | Isaacson et al. | |
| 5,596,283 A | 1/1997 | Mellitz et al. | |
| 5,626,146 A | 5/1997 | Barber et al. | |
| 5,679,022 A | 10/1997 | Cappa et al. | |
| 5,704,355 A | 1/1998 | Bridges | |
| 5,718,231 A | 2/1998 | Dewhurst et al. | |
| 5,732,710 A | 3/1998 | Rabinovich et al. | |
| 5,735,284 A | 4/1998 | Tsoglin et al. | |
| 5,746,214 A | 5/1998 | Brown et al. | |
| 5,759,159 A | 6/1998 | Masreliez | |
| 5,788,643 A | 8/1998 | Feldman | |
| 5,800,350 A | 9/1998 | Coppleson et al. | |
| 5,807,251 A | 9/1998 | Wang et al. | |
| 5,807,270 A | 9/1998 | Williams | |
| 5,807,272 A | 9/1998 | Kun et al. | |
| 5,810,742 A | 9/1998 | Pearlman | |
| 5,876,353 A | 3/1999 | Riff | |
| 5,906,614 A | 5/1999 | Stern et al. | |
| 5,919,142 A | 7/1999 | Boone et al. | |
| 5,957,861 A | 9/1999 | Combs et al. | |
| 6,006,125 A | 12/1999 | Kelly et al. | |
| 6,011,992 A | 1/2000 | Hubbard et al. | |
| 6,015,389 A | 1/2000 | Brown | |
| 6,018,677 A | 1/2000 | Vidrine et al. | |
| 6,026,323 A | 2/2000 | Skladnev et al. | |
| 6,122,544 A | 9/2000 | Organ | |
| 6,125,297 A | 9/2000 | Siconolfi | |
| 6,142,949 A | 11/2000 | Ubby | |
| 6,151,520 A | 11/2000 | Combs | |
| 6,151,523 A | 11/2000 | Rosell Ferrer et al. | |
| 6,173,003 B1 | 1/2001 | Whikehart et al. | |
| 6,208,890 B1 | 3/2001 | Sarrazin et al. | |
| 6,228,033 B1 | 5/2001 | Koobi et al. | |
| 6,233,473 B1 | 5/2001 | Shepherd et al. | |
| 6,236,886 B1 | 5/2001 | Cherepenin et al. | |
| 6,248,083 B1 | 6/2001 | Smith et al. | |
| 6,256,532 B1 | 7/2001 | Cha | |
| 6,292,690 B1 | 9/2001 | Petrucelli et al. | |
| 6,339,722 B1 | 1/2002 | Heethaar et al. | |
| 6,354,996 B1 | 3/2002 | Drinan et al. | |
| 6,432,045 B2 * | 8/2002 | Lemperle .................... 600/135 |
| 6,469,732 B1 | 10/2002 | Chang et al. | |
| 6,472,888 B2 | 10/2002 | Oguma et al. | |
| 6,496,725 B2 | 12/2002 | Kamada et al. | |
| 6,497,659 B1 | 12/2002 | Rafert | |
| 6,511,438 B2 | 1/2003 | Bernstein et al. | |
| 6,512,949 B1 | 1/2003 | Combs et al. | |
| 6,532,384 B1 | 3/2003 | Fukuda | |
| 6,551,252 B2 | 4/2003 | Sackner et al. | |
| 6,556,001 B1 | 4/2003 | Wiegand et al. | |
| 6,560,480 B1 | 5/2003 | Nachaliel et al. | |
| 6,561,986 B2 | 5/2003 | Baura et al. | |
| 6,569,160 B1 | 5/2003 | Goldin et al. | |
| 6,584,348 B2 | 6/2003 | Glukhovsky | |
| 6,602,201 B1 | 8/2003 | Hepp et al. | |
| 6,615,077 B1 | 9/2003 | Zhu et al. | |
| 6,618,616 B2 | 9/2003 | Iijima et al. | |
| 6,623,312 B2 | 9/2003 | Merry et al. | |
| 6,625,487 B2 | 9/2003 | Herleikson | |
| 6,631,292 B1 | 10/2003 | Liedtke | |
| 6,633,777 B2 | 10/2003 | Szopinski | |
| 6,636,754 B1 | 10/2003 | Baura et al. | |
| 6,643,543 B2 | 11/2003 | Takehara et al. | |
| 6,714,813 B2 | 3/2004 | Ishigooka et al. | |
| 6,714,814 B2 | 3/2004 | Yamada et al. | |
| 6,723,049 B2 | 4/2004 | Skladnev et al. | |
| 6,724,200 B2 | 4/2004 | Fukuda | |
| 6,725,089 B2 | 4/2004 | Komatsu et al. | |
| 6,753,487 B2 | 6/2004 | Fujii et al. | |
| 6,760,617 B2 | 7/2004 | Ward et al. | |
| 6,768,921 B2 | 7/2004 | Organ et al. | |

(56) References Cited

U.S. PATENT DOCUMENTS

| | | |
|---|---|---|
| 6,788,966 B2 * | 9/2004 | Kenan ................ A61B 5/0536 600/372 |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 6,980,852 B2 | 12/2005 | Jersey-Willuhn et al. |
| 7,096,061 B2 | 8/2006 | Arad |
| 7,122,012 B2 | 10/2006 | Bouton et al. |
| 7,130,680 B2 | 10/2006 | Kodama et al. |
| 7,148,701 B2 | 12/2006 | Park et al. |
| 7,149,573 B2 | 12/2006 | Wang |
| 7,164,522 B2 | 1/2007 | Kimura et al. |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,206,630 B1 | 4/2007 | Tarler |
| 7,212,852 B2 | 5/2007 | Smith et al. |
| 7,214,107 B2 | 5/2007 | Powell et al. |
| 7,233,823 B2 | 6/2007 | Simond et al. |
| 7,251,524 B1 | 7/2007 | Hepp et al. |
| 7,270,580 B2 | 9/2007 | Bradley et al. |
| D557,809 S | 12/2007 | Neverov |
| 7,353,058 B2 | 4/2008 | Weng et al. |
| 7,390,303 B2 | 6/2008 | Dafni |
| 7,457,660 B2 | 11/2008 | Smith et al. |
| 7,477,937 B2 | 1/2009 | Iijima et al. |
| D603,051 S | 10/2009 | Causevic |
| 7,706,872 B2 | 4/2010 | Min et al. |
| 7,733,224 B2 | 6/2010 | Tran |
| 7,749,013 B2 | 7/2010 | Sato et al. |
| 7,907,997 B2 | 3/2011 | Stahmann et al. |
| D641,886 S | 7/2011 | Causevic |
| D647,208 S | 10/2011 | Rothman |
| D669,186 S | 10/2012 | Gozani |
| D669,187 S | 10/2012 | Gozani |
| D674,096 S | 1/2013 | Gaw |
| 8,467,865 B2 | 6/2013 | Gregory |
| D718,458 S | 11/2014 | Vosch |
| D719,660 S | 12/2014 | Vosch |
| D728,801 S | 5/2015 | Machon |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson |
| 2001/0025139 A1 | 9/2001 | Pearlman |
| 2001/0049479 A1 | 12/2001 | Szopinski |
| 2001/0051774 A1 | 12/2001 | Littrup et al. |
| 2002/0022787 A1 | 2/2002 | Takehara et al. |
| 2002/0035334 A1 | 3/2002 | Meij |
| 2002/0072682 A1 | 6/2002 | Hopman et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0109621 A1 | 8/2002 | Khair et al. |
| 2002/0111559 A1 | 8/2002 | Kurata |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0163408 A1 | 11/2002 | Fujii et al. |
| 2002/0194419 A1 | 12/2002 | Rajput et al. |
| 2003/0004403 A1 | 1/2003 | Drinan et al. |
| 2003/0004433 A1 | 1/2003 | Hirschman |
| 2003/0023184 A1 | 1/2003 | Pitts-Crick et al. |
| 2003/0028221 A1 | 2/2003 | Zhu et al. |
| 2003/0050570 A1 | 3/2003 | Kodama |
| 2003/0068914 A1 | 4/2003 | Merry et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0216661 A1 * | 11/2003 | Davies .................. 600/547 |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0054298 A1 | 3/2004 | Masuo et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0116819 A1 | 6/2004 | Alt |
| 2004/0158167 A1 | 8/2004 | Smith et al. |
| 2004/0167423 A1 | 8/2004 | Pillon et al. |
| 2004/0171691 A1 | 9/2004 | Smith |
| 2004/0171961 A1 * | 9/2004 | Smith et al. .................. 600/547 |
| 2004/0171963 A1 | 9/2004 | Takehara |
| 2004/0181164 A1 | 9/2004 | Smith et al. |
| 2004/0186392 A1 | 9/2004 | Ward et al. |
| 2004/0204658 A1 | 10/2004 | Dietz et al. |
| 2004/0210150 A1 | 10/2004 | Virtanen |
| 2004/0210158 A1 | 10/2004 | Organ et al. |
| 2004/0234113 A1 | 11/2004 | Miga |
| 2004/0236202 A1 | 11/2004 | Burton |
| 2004/0242989 A1 | 12/2004 | Zhu et al. |
| 2004/0252870 A1 | 12/2004 | Reeves et al. |
| 2004/0253652 A1 | 12/2004 | Davies |
| 2004/0260167 A1 | 12/2004 | Leonhardt et al. |
| 2004/0267344 A1 | 12/2004 | Stett et al. |
| 2005/0033281 A1 | 2/2005 | Bowman et al. |
| 2005/0039763 A1 | 2/2005 | Kraemer et al. |
| 2005/0070778 A1 | 3/2005 | Lackey et al. |
| 2005/0080460 A1 | 4/2005 | Wang et al. |
| 2005/0098343 A1 | 5/2005 | Fukuda |
| 2005/0101875 A1 | 5/2005 | Semler et al. |
| 2005/0107719 A1 | 5/2005 | Arad (Abboud) et al. |
| 2005/0113704 A1 | 5/2005 | Lawson et al. |
| 2005/0117196 A1 | 6/2005 | Kimura et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0192511 A1 | 9/2005 | Shiokawa |
| 2005/0201598 A1 | 9/2005 | Harel et al. |
| 2005/0203435 A1 | 9/2005 | Nakada |
| 2005/0203436 A1 * | 9/2005 | Davies .................. 600/547 |
| 2005/0215918 A1 | 9/2005 | Frantz et al. |
| 2005/0228309 A1 | 10/2005 | Fisher et al. |
| 2005/0261743 A1 | 11/2005 | Kroll |
| 2005/0283091 A1 | 12/2005 | Kink et al. |
| 2006/0004300 A1 | 1/2006 | Kennedy |
| 2006/0041280 A1 | 2/2006 | Stahmann et al. |
| 2006/0047189 A1 | 3/2006 | Takehara |
| 2006/0064029 A1 | 3/2006 | Arad (Abboud) et al. |
| 2006/0085048 A1 | 4/2006 | Cory et al. |
| 2006/0085049 A1 | 4/2006 | Cory et al. |
| 2006/0100532 A1 | 5/2006 | Bae |
| 2006/0110962 A1 | 5/2006 | Powell et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0128193 A1 | 6/2006 | Bradley et al. |
| 2006/0135886 A1 | 6/2006 | Lippert et al. |
| 2006/0151815 A1 | 7/2006 | Graovac et al. |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0247739 A1 | 11/2006 | Wahlstrand et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2006/0293609 A1 | 12/2006 | Stahmann et al. |

(56) References Cited

U.S. PATENT DOCUMENTS

| | | |
|---|---|---|
| 2007/0007975 A1 | 1/2007 | Hawkins et al. |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0106342 A1 | 5/2007 | Schumann |
| 2007/0156061 A1 | 7/2007 | Hess |
| 2008/0001608 A1 | 1/2008 | Saulnier et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0064981 A1 | 3/2008 | Gregory |
| 2008/0205717 A1 | 8/2008 | Reeves et al. |
| 2008/0252304 A1 | 10/2008 | Woo et al. |
| 2008/0262375 A1* | 10/2008 | Brown et al. .................. 600/547 |
| 2008/0270051 A1 | 10/2008 | Essex et al. |
| 2008/0287823 A1 | 11/2008 | Chetham |
| 2008/0319336 A1 | 12/2008 | Ward et al. |
| 2009/0043222 A1 | 2/2009 | Chetham |
| 2009/0054952 A1 | 2/2009 | Glukhovsky et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0084674 A1 | 4/2009 | Holzhacker et al. |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0264776 A1 | 10/2009 | Vardy |
| 2009/0287102 A1 | 11/2009 | Ward |
| 2009/0306535 A1* | 12/2009 | Davies et al. .................. 600/547 |
| 2009/0318778 A1 | 12/2009 | Dacso et al. |
| 2010/0100003 A1 | 4/2010 | Chetham et al. |
| 2010/0109739 A1 | 5/2010 | Ironstone et al. |
| 2010/0145164 A1 | 6/2010 | Howell |
| 2010/0168530 A1 | 7/2010 | Chetham et al. |
| 2010/0234701 A1 | 9/2010 | Cho et al. |
| 2011/0025348 A1* | 2/2011 | Chetham et al. .............. 324/649 |
| 2011/0060239 A1 | 3/2011 | Gaw |
| 2011/0118619 A1 | 5/2011 | Burton et al. |
| 2011/0251513 A1 | 10/2011 | Chetham |

FOREIGN PATENT DOCUMENTS

| | | |
|---|---|---|
| CA | 2615845 A1 | 1/2007 |
| CA | 2638958 | 11/2011 |
| CN | 1180513 A | 5/1998 |
| CN | 1236597 A | 12/1999 |
| CN | 1329875 A | 1/2002 |
| CN | 1366694 A | 8/2002 |
| CN | 101385203 A | 3/2009 |
| DE | 2912349 A1 | 10/1980 |
| EP | 249823 A1 | 12/1987 |
| EP | 349043 A2 | 1/1990 |
| EP | 357309 A2 | 3/1990 |
| EP | 377887 A1 | 7/1990 |
| EP | 581073 A2 | 2/1994 |
| EP | 662311 A1 | 7/1995 |
| EP | 865763 | 9/1998 |
| EP | 869360 A2 | 10/1998 |
| EP | 1078597 A2 | 2/2001 |
| EP | 1080686 A1 | 3/2001 |
| EP | 1112715 A1 | 7/2001 |
| EP | 1114610 A1 | 7/2001 |
| EP | 1146344 A1 | 10/2001 |
| EP | 1177760 A1 | 2/2002 |
| EP | 1219937 A1 | 7/2002 |
| EP | 1238630 A2 | 9/2002 |
| EP | 1247487 A1 | 10/2002 |
| EP | 1283539 A1 | 2/2003 |
| EP | 1329190 A1 | 7/2003 |
| EP | 1338246 A1 | 8/2003 |
| EP | 1452131 A1 | 9/2004 |
| EP | 1629772 A1 | 3/2006 |
| FR | 2486386 A1 | 1/1982 |
| FR | 2748928 A1 | 11/1997 |
| GB | 2131558 A | 6/1984 |
| GB | 2260416 A | 4/1993 |
| GB | 2426824 A | 12/2006 |
| JP | 04-096733 A | 3/1992 |
| JP | 06-000168 A | 1/1994 |
| JP | 8191808 A | 7/1996 |
| JP | 9051884 A | 2/1997 |
| JP | 9220209 A | 8/1997 |
| JP | 10000185 A | 1/1998 |
| JP | 10014898 A | 1/1998 |
| JP | 10014899 A | 1/1998 |
| JP | 10-080406 A | 3/1998 |
| JP | 10-225521 A | 8/1998 |
| JP | 11070090 A | 3/1999 |
| JP | 2000107138 A | 4/2000 |
| JP | 2000139867 A | 5/2000 |
| JP | 2001037735 A | 2/2001 |
| JP | 2001-070273 A | 3/2001 |
| JP | 2001061804 A | 3/2001 |
| JP | 2001-224568 A | 8/2001 |
| JP | 2001321352 A | 11/2001 |
| JP | 2002-350477 | 4/2002 |
| JP | 2002-238870 A | 8/2002 |
| JP | 2002330938 A | 11/2002 |
| JP | 2003-230547 A | 8/2003 |
| JP | 2003-075487 | 12/2003 |
| JP | 2004-61251 A | 2/2004 |
| JP | 2005099186 A | 4/2005 |
| JP | 2005-143786 A | 6/2005 |
| JP | 2008022995 A | 2/2008 |
| NL | 001019789 C2 | 7/2003 |
| RU | 2112416 C1 | 6/1998 |
| RU | 2138193 C1 | 9/1999 |
| SU | 1132911 A1 | 1/1985 |
| WO | 8807392 A1 | 10/1988 |
| WO | 9318821 A1 | 9/1993 |
| WO | 9410922 A1 | 5/1994 |
| WO | 9601586 A1 | 1/1996 |
| WO | 9612439 A1 | 5/1996 |
| WO | 9632652 A1 | 10/1996 |
| WO | 9711638 A2 | 4/1997 |
| WO | 9714358 A1 | 4/1997 |
| WO | 97/24156 A1 | 7/1997 |
| WO | 9743000 A1 | 11/1997 |
| WO | 9806328 A1 | 2/1998 |
| WO | 9823204 A1 | 6/1998 |
| WO | 9833553 A1 | 8/1998 |
| WO | 9851211 A1 | 11/1998 |
| WO | 9854792 A1 | 12/1998 |
| WO | 0019886 A1 | 4/2000 |
| WO | 0040955 A1 | 7/2000 |
| WO | 0079255 A1 | 12/2000 |
| WO | 0127605 A1 | 4/2001 |
| WO | 0150954 A1 | 7/2001 |
| WO | 0167098 A1 | 9/2001 |
| WO | 01/78831 A2 | 10/2001 |
| WO | 0182323 A1 | 11/2001 |
| WO | 02/47548 A1 | 6/2002 |
| WO | 02-053028 A2 | 7/2002 |
| WO | 02062214 A1 | 8/2002 |
| WO | 02094096 A1 | 11/2002 |
| WO | 02/100267 A1 | 12/2002 |
| WO | 2004000115 A1 | 12/2003 |
| WO | 2004-032738 A1 | 4/2004 |
| WO | 2004026136 A1 | 4/2004 |
| WO | 2004030535 A1 | 4/2004 |
| WO | 2004032738 A1 | 4/2004 |
| WO | 2004-043252 A1 | 5/2004 |
| WO | 2004-047636 A1 | 6/2004 |
| WO | 2004047635 A1 | 6/2004 |
| WO | 2004047636 A1 | 6/2004 |
| WO | 2004047638 A1 | 6/2004 |
| WO | 2004048983 A1 | 6/2004 |
| WO | 2004049936 A2 | 6/2004 |
| WO | 2004083804 A2 | 9/2004 |

(56) References Cited

FOREIGN PATENT DOCUMENTS

| WO | 2004084723 A1 | 10/2004 |
|---|---|---|
| WO | 2004084724 A1 | 10/2004 |
| WO | 2004-098389 A2 | 11/2004 |
| WO | 2005010640 A2 | 2/2005 |
| WO | 2005018432 A2 | 3/2005 |
| WO | 2005027717 A2 | 3/2005 |
| WO | 2005051194 A1 | 6/2005 |
| WO | 2005084539 A1 | 9/2005 |
| WO | 2005122881 A1 | 12/2005 |
| WO | 2005122888 A1 | 12/2005 |
| WO | 2006/129116 A1 | 12/2006 |
| WO | 2006129108 A1 | 12/2006 |
| WO | 2007002991 A1 | 1/2007 |
| WO | 2007002992 A1 | 1/2007 |
| WO | 2007002993 A1 | 1/2007 |
| WO | 2007009183 A1 | 1/2007 |
| WO | 2007014417 A1 | 2/2007 |
| WO | 2007041783 A1 | 4/2007 |
| WO | 2007-056493 A1 | 5/2007 |
| WO | 2007089278 A1 | 8/2007 |
| WO | 2008064426 A1 | 6/2008 |
| WO | 2008119166 A1 | 10/2008 |
| WO | 2008138062 A1 | 11/2008 |
| WO | 2009/018620 A1 | 2/2009 |
| WO | 2009036369 A1 | 3/2009 |
| WO | 2009059351 A1 | 5/2009 |
| WO | 2009100491 A1 | 8/2009 |
| WO | 2010051600 A1 | 5/2010 |
| WO | 2010060152 A1 | 6/2010 |
| WO | 2011022068 A1 | 2/2011 |
| WO | 2011050393 A1 | 5/2011 |
| WO | 2011075769 A1 | 6/2011 |

OTHER PUBLICATIONS

De Lorenzo et al.; Predicting body cell mass with bioimpedance by using theoretical methods: a technological review; J. Appl. Physiol., 1997; 82(5): 1542-58.
Zhu et al.; Segment-specific resistivity improves body fluid volume estimates from bioimpedance spectroscopy in hemodialysis patients; J. Appl. Physiol., 2005; 100: 717-724.
Liu et al.; Primary multi-frequency data analyze in electrical impedance scanning; Proceedings of the IEEE-EMBS 2005, 27th Annual Int'l Conference of the Engineering in Med. and Biology Soc., Shanghai, China, Sep. 4, 2005; 1504-1507.
Gudivaka et al.; Single- and multifrequency models for bioelectrical impedance analysis of body water compartments; J. Appl. Physiol., 1999; 87(3): 1087-96.
Thomas et al.; Bioimpedance Spectrometry in the determination of Body Water Compartments: Accuracy and Clinical Significance; Applied Radiation and Isotopes, Elsevier, Oxford, GB, 1998; 49(5-6): 447-455.
Cornish et al.; Data analysis in multiple-frequency bioelectrical impedance analysis; Physiological Measurement, Institute of Physics Publishing, Bristol, GB, 1998; 19(2): 275-283.
Ulgen et al.; Electrical Parameters of Human Blood; Database accession No. 6408967 & Proceedings of the 20th Annual International Conference of the IEEE Engineering in Medicine and Biology Soc., 1998; 20(6): 2983-2986, IEEE Piscataway, NJ.
Gerth et al., A computer-based bioelectrical impedance spectroscopic system for noninvasive assesment of compartmental fluid redistribution, 1990; 446-453.
Kanai et al.; Electrical measurement of fluid distribution in legs and arms; Medical Progress through Technology, 1987; 12: 159-170.
Bracco et al.; Bedside determination of fluid accumulation after cardiac surgery usign segmental bioelectrical impedance; Critical Care Medicine, 1998; 26(6): 1065-1070.
Chiolero et al.; Assessment of changes in body water by bioimpedance in acutely ill surgical patients; Intensive Care Medicine, 1992; 18: 322-326.

Chumlea et al.; Bioelectrical impedance and body composition: present status and future directions; Nutrition Reviews, 1994; 52(4): 123-131.
Cornish et al.; Bioelectrical impedance for monitoring the efficacy of lymphoedema treatment programmes; Breast Cancer Research and Treatment, 1996; 38: 169-176.
Cornish et al.; Quantification of lymphoedema using multi-frequency bioimpedance; Applied Radiation and Isotopes, Elsevier, Oxford, GB, 1998; 49(5/6): 651-652.
De Luca et al.; Use of low-frequency electrical impedance mesurements to determine phospholipid content in amniotic fluid; Physics in Medicine and Biology, 1996; 41: 1863-1869.
Derwent; Abstract No. 97-474414, JP 09 220209 A (Sekisui Chem, Ind. Co. Ltd.), Aug. 26, 1997; Abstract.
Derwent; Abstract No. 98-138541, JP 10 014898 A (Sekisui Chem, Ind. Co. Ltd.), Jan. 20, 1998; Abstract.
Derwent; Abstract No. 99-247542, JP 11 070090 A (Sekisui Chem. Ind. Co. Ltd.), Mar. 16, 1999; Abstract.
Deurenberg et al.; Multi-frequency bioelectrical impedance: a comparison between the Cole-Cole modelling and Hanai equations with the classical impedance index approach; Annals of Human Biology, 1996; 23(1): 31-41.
Kim et al.; Bioelectrical impedance changes in regional extracellular fluid alterations; Electromyography and Clinical Neurophysiology, 1997; 37: 297-304.
Rigaud et al.; Biolectrical impedance techniques in medicine; Critical Reviews in Biomedical Engineering, 1996; 24 (4-6): 257-351.
Steijaert et al.; The use of multi-frequency impedance to determine total body water and extracellular water in obese and lean female individuals; International Journal of Obesity, 1997; 21: 930-934.
Ward et al.; Multi-frequency bioelectrical impedance augments the diagnosis and management of lymphoedema in post-mastectomy patients; European J. of Clin. Investigation, 1992; 22: 751-754.
European Search Report for EP 07718972.8-1265 / 2020918 (Impedimed, Ltd.), mailed on Mar. 2, 2010, 4 pages.
Derwent; Abstract No. 98-138542, JP 10 014899 A (Sekisui Chem, Ind. Co. Ltd.), Feb. 20, 1998; Abstract.
Ellis et al.; Human hydrometry: comparison of multifrequency biolectrical impedance with 2H2O and bromine dilution; Journal of Applied Physiology; 1998; 85(3): 1056-1062.
Jones et al.; Extracellular fluid volume determined by bioelectric impedance and serum albumin in CAPD patients; Nephrology Dialysis Transplantation; 1998; 13: 393-397.
Thomas B.J.; Future technologies; Asia Pacific Journal Clinical Nutrition; 1995; 4: 157-159.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.
Woodrow et al.; Effects of icodextrin in automated peritoneal dialysis on blood pressure and bioelectrical impedance analysis; Nephrology Dialysis Transplantation; 2000; 15: 862-866.
Boulier et al.; Fat-Free Mass Estimation by Two Electrode Impedance Method; American Journal of Clinical Nutrition; 1990; 52: 581-585.
McDougal et al.; Body Composition Measurements from Whole Body Resistance and Reactance; Surgical Forum; 1986; 36: 43-44.
Tedner, B.; Equipment using Impedance Technique for Automatic Recording of Fluid-Volume Changes during Hemodialysis; Medical & Biological Engineering & Computing; 1983; 285-290.
Lukaski et al.; Estimation of Body Fluid Volumes using Tetrapolar Bioelectrical Impedance Measurements; Aviation, Space, and Environmental Medicine; Dec. 1988; 1163-1169.
Lozano et al.; Two-frequency impedance plethysmograph: real and imaginary parts; Medical & Biological Engineering & Computing; Jan. 1990; 28(1): 38-42.
Chaudary et al.; Dielectric Properties of Normal & Malignant Human Breast Tissues at Radiowave and Microwave Frequencies; Indian Journal of Biochemistry & Biophysics; 1984; 21(1): 76-79.

(56) References Cited

OTHER PUBLICATIONS

Jossinet et al.; A study for breast imaging with a circular array of impedance electrodes; Proc. Vth Int. Conf. Bioelectrical Impedance, 1981, Tokyo, Japan; 1981; 83-86.

Jossinet et al.; Technical Implementation and Evaluation of a Bioelectrical Breast Scanner; Proc. 10.supth Int. Conf. IEEE Engng. Med. Biol., 1988, New Orleans, USA (Imped. Imaging II); 1988; 1: 289.

Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.

Pethig et al.; The Passive Electrical Properties of Biological Systems: Their Significance in Physiology, Biophysics and Biotechnology; Physics in Medicine and Biology; 1987; 32: 933-970.

Piperno et al.; Breast Cancer Screening by Impedance Measurements; Frontiers of Medical & Biological Engineering; 1990; 2: 111-117.

Skidmore et al.; A Data Collection System for Gathering Electrical Impedance Measurements from the Human Breast; Clinical Physics Physiological Measurement; 1987; 8: 99-102.

Sollish et al.; Microprocessor-assisted Screening Techniques; Israel Journal of Medical Sciences; 1981; 17: 859-864.

Surowiec et al.; Dielectric Properties of Breast Carcinima and the Surrounding Tissues; IEEE Transactions on Biomedical Engineering; 1988; 35: 257-263.

Al-Hatib, F.; Patient Instrument Connection Errors in Bioelectrical Impedance Measurement; Physiological Measurement; May 2, 1998; 19(2): 285-296.

Gersing, E.; Impedance Spectroscopy on Living Tissue for Determination of the State of Organs; Bioelectrochemistry and Bioenergetics; 1998; 45: 145-149.

Mattar, J.A.; Application of Total Body Impedance to the Critically Ill Patient; New Horizons; 1996; 4(4): 493-503.

Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.

U.S. Appl. No. 12/516,876, filed Jul. 1, 2010, Chetham.
U.S. Appl. No. 12/596,833, filed Jun. 17, 2010, Ward.
U.S. Appl. No. 12/600,244, Chetham.
U.S. Appl. No. 12/672,893, filed Feb. 24, 2011, Cornish.
U.S. Appl. No. 10/767,825, filed Sep. 23, 2004, Ward.
U.S. Appl. No. 12/302,914, filed Apr. 8, 2010, McGree.
U.S. Appl. No. 13/128,631, Essex.

Thomas et al.; Bioelectrical impedance analysis for measurement of body fluid volumes—A review; Journal of Clinical Engineering; 1992; 17(16): 505-510.

Ward et al.; There is a better way to measure Lymphedema; National Lymphedema Network Newsletter; Oct. 1995; 7 (4): 89-92.

Cornish et al.; Alteration of the extracellular and total body water volumes measured by multiple frequency bioelectrical impedance analysis; Nutrition Research; 1994; 14(5): 717-727.

Cornish et al.; Early diagnosis of lymphedema using multiple frequency bioimpedance; Lymphology; Mar. 2001; 34: 2-11.

Cornish et al.; Early diagnosis of lymphoedema in postsurgery breast cancer patients; Annals New York Academy of Sciences; May 2000; 571-575.

Brown et al.; Relation between tissue structure and imposed electrical current flow in cervical neoplasia; The Lancet; Mar. 11, 2000; 355 (9207): 892-895.

Iacobellis, G. et al.; Influence of excess fat on cardiac morphology and function: Study in Uncomplicated obesity; Obesity Research; Aug. 8, 2002; 10 (8): 767-773.

Bella, J. N. et al.; Relations of left ventricular mass to fat-free and adipose body mass: The Strong Heart Study; Circulation; Dec. 12, 1998; 98: 2538-2544.

Yoshinaga, M. et al.; Effect of total adipose weight and systemic hypertension on left ventricular mass in children; American Journal of Cardiology; Oct. 15, 1995; 76: 785-787.

Karason, K. et al.; Impact of blood pressure and insulin on the relationship between body fat and left ventricular structure; European Heart Journal; Jan. 1, 2003; 24: 1500-1505.

Abdullah M. Z.; Simulation of an inverse problem in electrical impedance tomography using resistance electrical network analogues; International Journal of Electrical Engineering Education; Oct. 1999; 36 (4): 311-324.

Dines et al.; Analysis of electrical conductivity imaging; Geophysics; Jul. 1981; 46 (7): 1025-1036.

Osterman et al.; Multifrequency electrical impedance imaging: preliminary in vivo experience in breast; Physiological Measurement; Feb. 2000; 21 (1): 99-109.

Ward et al.; Determination of Cole parameters in multiple frequency bioelectrical impedance analysis using only the measurement of impedances; Four-frequenct fitting; Physiological Measurement; Sep. 2006; 27 (9): 839-850.

Bernstein; A new stroke volume equation for thoracic electrical bio impedance; Critical Care Medicine; 1986; vol. 14; pp. 904-909.

McAdams et al.; Tissue Impedance: a historical overview; Physiological Measurement, Institute of Physics Publishing, Bristol, GB; 16 (3A); pp. 1l-A13; Aug. 1, 1995.

D'Entremont et al. "Impedance spectroscopy: an accurate method of differentiating between viable and ischaemic or infarcted muscle tissue" Med. Biol. Eng. Comput., 2002, 40: 380-87.

Zhu et al., "Dynamics of segmental extracellular volumes during changes in body position by bioimpedance analysis"; J. App. Physiol.; 1998, vol. 85, pp. 497-504.

McCullagh, W. A., et al., Bioelectrical impedance analysis measures the ejection fraction of the calf muscle pump, IFMBE Proceedings, 2007; vol. 17, p. 619.

Scharfetter, Effect of postural changes on the reliability of volume estimations from bioimpedance spectroscopy data, Kidney International Apr. 1997, vol. 51, No. 4, pp. 1078-1087.

Ezenwa, Multiple frequency system for body composition measurement, Medical Informatics, Ethics, Cardiology, Instrumentation., Proceedings of the Annual International Conference of the Engineering in Medicine and Biology Society, Oct. 28, 1993, vol. 15, Part 02.

Yamakoshi, Non-Invasive Cardiovascular Hemodynamic Measurements, Sensors in Medicine and Health Care, 2004, pp. 107-160.

Ivorra, Bioimpedance dispersion width as a parameter to monitor living tissues, Physiological Measurement, 2005, vol. 26, S165-S173.

* cited by examiner

Fig. 6A
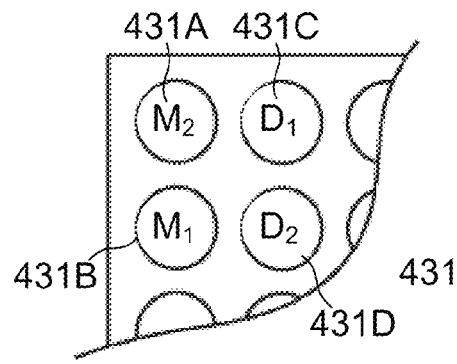
Fig. 6B
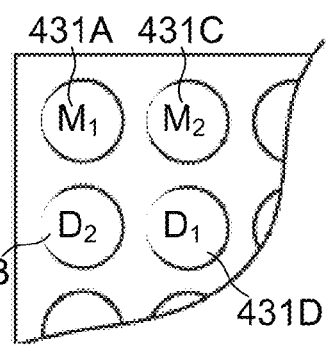
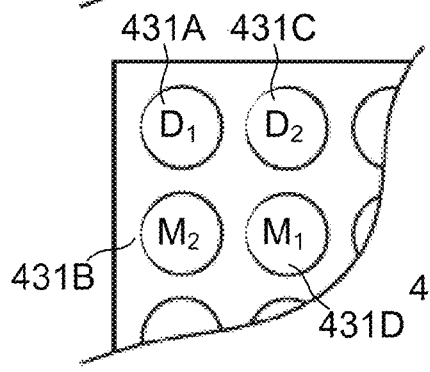
Fig. 6C
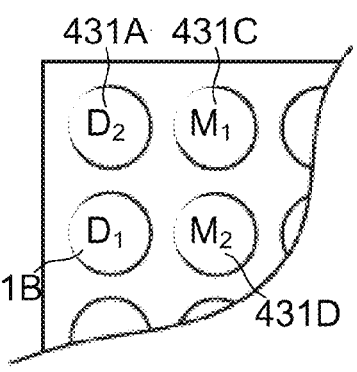
Fig. 6D
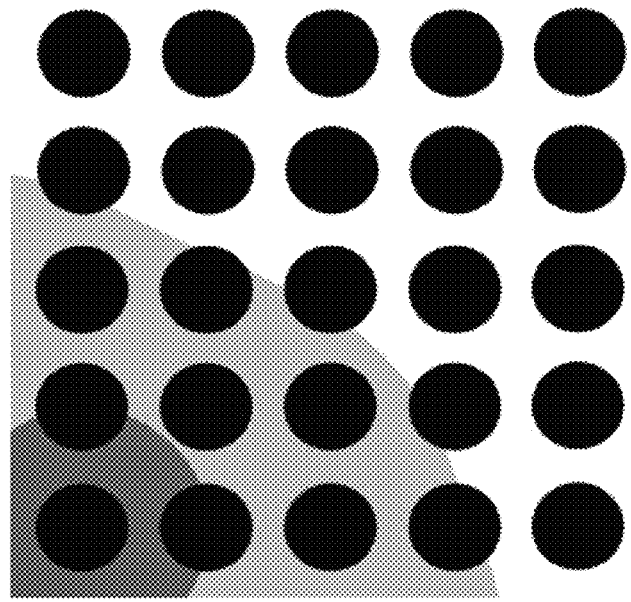
Fig. 7

IMPEDANCE MEASUREMENT PROCESS

BACKGROUND OF THE INVENTION

The present invention relates to a method and apparatus for performing impedance measurements, and in particular to performing multiple impedance measurements at a given site to determine an indicator indicative of the presence, absence or degree of anomalies such as tissue lesions.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Presently, the detection of the existence of certain biological lesions or anomalies within a region requires the use of methods which are not only invasive but also require a sample of the region to be removed and sent away for biological testing.

For example, in the detection of cervical cancer, it is often the case that a patient will undergo several tests typically beginning with a Pap Smear (the Papanicolaou test) which includes a tool that is used to gather cells from the cervical region. If the Pap Smear result is positive, a patient may then undergo biopsies which will require the removal of a sample area of the suspected region.

It will be appreciated that these methods can cause severe discomfort for persons undergoing the tests, and furthermore, the tests may not always provide a high degree of accuracy.

One existing technique for determining biological parameters relating to a subject, such as fluid levels, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema, or other conditions which affect body habitus.

GB2426824 describes a probe for measuring the electrical impedance of human or animal body tissue comprises a housing and at least two electrodes mounted on the surface of the housing. Contained within the housing are: a current source coupled to the electrodes, a controller to control the current source to drive a current between the electrodes, a voltmeter to measure potential difference between the electrodes, and a communication circuit for wirelessly transmitting the measured potential difference to a remote device. The probe may also include a processor to calculate tissue impedance from the measured potential difference, in which case the communication circuit transmits the calculated impedance. Wireless telemetry may be via an optical or radio frequency (RF) connection, for example using an infra red transmitter. The transmission of data without the use of a wired connection improves measurement accuracy due to the removal of the parasitic capacitances arising from cable connections. The probe may be used for cancer screening. A method of measuring impedance is also disclosed.

SUMMARY OF THE PRESENT INVENTION

The present invention seeks to substantially overcome, or at least ameliorate, one or more disadvantages of existing arrangements.

In a first broad form, the present invention seeks to provide apparatus for use in performing impedance measurements on a subject, the apparatus including:
 a) a probe having a plurality of electrodes, the probe being configured to allow at least some of the electrodes to be in contact with at least part of the subject; and,
 b) a processing system for:
  i) determining at least one first impedance value, measured at a site using a first electrode configuration;
  ii) determining at least one second impedance value, measured at the site using a second electrode configuration; and,
  iii) determining an indicator indicative of the presence, absence or degree of an anomaly using the first and second impedance values.

Typically at least part of the probe is configured to be inserted into the subject so that at least some of the electrodes are in contact with cervical tissues.

Typically the probe includes:
 a) a probe portion including the plurality of electrodes; and,
 b) a handle portion.

Typically the probe portion is removably attached to the handle portion.

Typically the probe portion is for insertion into the subject.

Typically the handle portion includes at least one of:
 a) at least part of the processing system;
 b) a signal generator for applying drive signals to the electrodes;
 c) a sensor for determining measured signals at the electrodes;
 d) a multiplexer for selectively connecting the electrodes to the signal generator and the sensor; and,
 e) a capacitance cancelling circuit.

Typically the processing system includes a first processing system and a second processing system and wherein at least one of the first and second processing systems is provided in the handle portion.

Typically the apparatus includes:
 a) a signal generator for applying drive signals to the subject using drive electrodes; and,
 b) a sensor for determining measured signals using measurement electrodes.

Typically the apparatus includes a switching device for selectively interconnecting the signal generator and sensor to the electrodes.

Typically the apparatus includes a tetrapolar electrode arrangement, the first and second electrode configurations using a different configuration of drive and measurement electrodes.

Typically the apparatus includes an electrode array having a number of electrodes provided thereon, and wherein in use, selected ones of the electrodes are used as drive and measurement electrodes.

Typically the processing system:
 a) causes a first measurement to be performed at a site using first and second electrodes as drive electrodes and using third and fourth electrodes as measurement electrodes; and,
 b) causes a second measurement to be performed at the site using first and third electrodes as drive electrodes and using second and fourth electrodes as measurement electrodes.

Typically the processing system:
a) causes a measurement to be performed at a site using first and second electrodes as drive electrodes and using third and fourth electrodes as measurement electrodes; and,
b) causes a measurement to be performed at a second site using at least two of the first, second, third and fourth electrodes.

Typically the processing system:
a) causes a first measurement to be performed at a first site using first and second electrodes as drive electrodes and using third and fourth electrodes as measurement electrodes;
b) causes a second measurement to be performed at the first site using first and third electrodes as drive electrodes and using second and fourth electrodes as measurement electrodes;
c) causes a first measurement to be performed at a second site using third and fifth electrodes as drive electrodes and using fourth and sixth electrodes as measurement electrodes; and,
d) causes a second measurement to be performed at the second site using third and fourth electrodes as drive electrodes and using fifth and sixth electrodes as measurement electrodes.

Typically the apparatus includes a capacitance cancelling circuit for cancelling capacitance coupling between first and second electrodes.

Typically the capacitance cancelling circuit includes an inverting amplifier for coupling a signal generator output to a sensor input.

Typically the inverting amplifier applies a capacitance cancelling signal to the sensor input to thereby cancel any effective capacitance between the first electrode and the second electrode.

Typically an inverting amplifier output is coupled to the sensor input via at least one of:
a) a resistor;
b) a capacitor; and,
c) an inductor.

Typically at least one of a resistor and capacitor are adjustable, thereby allowing a capacitance cancelling signal applied to the sensor input to be controlled.

Typically the apparatus includes an input capacitance cancelling circuit for cancelling an effective input capacitance at a sensor input.

Typically the apparatus includes a feedback loop for connecting a sensor output to the sensor input.

Typically the feedback loop includes at least one of:
a) a resistor;
b) a capacitor; and,
c) an inductor.

Typically at least one of a resistor and capacitor are adjustable, thereby allowing a current flow from the sensor output to the sensor input to be controlled.

Typically the feedback loop applies an input capacitance cancelling signal to the sensor input to thereby cancel any effective capacitance at the sensor input.

Typically the processing system determines an impedance value for each of at least four electrode configurations.

Typically the apparatus includes a signal generator, a sensor, a switching device, and wherein the processing system controls the electrode configuration by:
a) selectively interconnecting the signal generator and electrodes using the switching device; and,
b) selectively interconnecting the sensor and electrodes using the switching device.

Typically the processing system:
a) causes at least one drive signals to be applied to the subject;
b) measures at least one induced signal across the subject; and,
c) determines at least one impedance value using an indication of the drive signal and the induced signal.

Typically the processing system:
a) determines impedance values at a number of different sites; and,
b) determines an impedance map using the impedance values at each site.

Typically the processing system:
a) determines the presence of an anomaly at any one of the sites; and,
b) determines the impedance map taking the anomaly into account.

Typically the processing system, for a site having an anomaly, at least one of:
a) excluding the site from the impedance map;
b) modifying the impedance value determined for the site.

Typically the processing system:
a) determines a difference between the first and second impedance values; and,
b) determines an anomaly using the determined difference.

Typically the processing system:
a) compares the difference to a reference; and,
b) determines an anomaly depending on the result of the comparison.

Typically the processing system, wherein the reference is a previously measured difference for the subject.

Typically the apparatus includes a store for storing the reference.

Typically the processing system:
a) compares first and second impedance values; and,
b) determines the presence, absence or degree of a biological anomaly using the results of the comparison.

Typically the impedance values are at least one of:
a) measured impedance values; and,
b) impedance parameter values derived from measured impedance values.

Typically the impedance parameter values include at least one of:
a) an impedance at infinite applied frequency ($R_\infty$);
b) an impedance at zero applied frequency ($R_0$); and,
c) an impedance at a characteristic frequency ($Z_c$).

Typically the processing system determines the impedance parameter values at least in part using the equation:

$$Z = R_\infty + \frac{R_0 - R_\infty}{1 + (j\omega\tau)^{(1-\alpha)}}$$

where: $R_\infty$=impedance at infinite applied frequency;
$R_0$=impedance at zero applied frequency;
$\omega$=angular frequency;
$\tau$ is the time constant of a capacitance circuit modelling the subject response; and,
$\alpha$ has a value between 0 and 1.

Typically the processing system:
a) causes at least one first impedance value to be measured at a site using a first electrode configuration; and,
b) causes at least one second impedance value to be measured at the site using a second electrode configuration.

Typically the apparatus includes a measuring device for performing impedance measurements, the measuring device including the processing system.

Typically the anomaly includes any one or a combination of:
  a) a tissue anomaly; and,
  b) an erroneous measurement.

Typically the tissue anomaly is a tissue lesion.

Typically the apparatus is used to detect the presence, absence, or degree of cervical cancer.

Typically the processing system is for:
  a) determining an indication of drive signals applied to the subject;
  b) determining an indication of measured signals determined using a sensor; and,
  c) using the indications to determine an impedance.

In a second broad form, the present invention seeks to provide a method for use in performing impedance measurements on a subject using a probe having a plurality of electrodes, the method including, in a processing system:
  a) determining at least one first impedance value, measured at a site using a first electrode configuration;
  b) determining at least one second impedance value, measured at the site using a second electrode configuration; and,
  c) determining an indicator indicative of the presence, absence or degree of an anomaly using the first and second impedance values.

In a third broad form, the present invention seeks to provide apparatus for use in performing impedance measurements on a subject, the apparatus including a probe having:
  a) an electrode array having a number of electrodes;
  b) a signal generator for generating drive signals;
  c) a sensor for sensing measured signals; and,
  d) a switching device;
  e) a processing system for selectively interconnecting the signal generator and the sensor to electrodes in the array using the switching device, thereby allowing:
    i) at least one first impedance value to be measured at a site using a first electrode configuration; and,
    ii) at least one second impedance value to be measured at the site using a second electrode configuration.

In a fourth broad form, the present invention seeks to provide apparatus for use in performing impedance measurements on a subject, the apparatus including:
  a) an electrode array having a number of electrodes;
  b) a signal generator for generating drive signals;
  c) a sensor for sensing measured signals; and,
  d) a switching device;
  e) a processing system for selectively interconnecting the signal generator and the sensor to electrodes in the array using the switching device, thereby allowing impedance measurements to be performed; and,
  f) a capacitance cancelling circuit for cancelling at least one of:
    i) capacitive coupling between first and second electrodes; and,
    ii) an effective capacitance at a sensor input.

Typically the processing system selectively interconnects the signal generator and the sensor to electrodes in the array using the switching device, thereby allowing:
  a) at least one first impedance value to be measured at a site using a first electrode configuration; and,
  b) at least one second impedance value to be measured at the site using a second electrode configuration.

In a fifth broad form, the present invention seeks to provide a method for use in performing impedance measurements on a subject, the method including, in a processing system:
  a) determining at least one first impedance value, measured at a site using a first electrode configuration;
  b) determining at least one second impedance value, measured at the site using a second electrode configuration; and,
  c) determining an indicator indicative the presence, absence or degree of an anomaly using the first and second impedance values, the indicator being used in the detection of cervical cancer.

Typically the method includes using a tetrapolar electrode arrangement, the first and second electrode configurations using a different configuration of drive and measurement electrodes.

Typically the method includes, in the processing system, determining an impedance value for each of four electrode configurations.

Typically the method uses apparatus including a signal generator, a sensor, a switching device and an electrode array having a number of electrodes, and wherein the method includes in the processing system, controlling the electrode configuration by:
  a) selectively interconnecting the signal generator and electrodes using the switching device; and,
  b) selectively interconnecting the sensor and electrodes using the switching device.

Typically the method includes, in the processing system:
  a) causing at least one drive signals to be applied to the subject;
  b) measuring at least one induced signal across the subject; and,
  c) determining at least one impedance value using an indication of the excitation signal and the induced signal.

Typically the method includes, in the processing system:
  a) determining impedance values at a number of different sites; and,
  b) determining an impedance map using the impedance values at each site.

Typically the method includes, in the processing system:
  a) determining the presence of an anomaly at any one of the sites; and,
  b) determining the impedance map taking the anomaly into account.

Typically the method includes, in the processing system, for a site having an anomaly, at least one of:
  a) excluding the site from the impedance map;
  b) modifying the impedance value determined for the site.

Typically the method includes, in the processing system:
  a) determining a difference between the first and second impedance values; and,
  b) determining an anomaly using the determined difference.

Typically the method includes, in the processing system:
  a) comparing the difference to a reference; and,
  b) determining an anomaly depending on the result of the comparison.

Typically the reference is a previously measured difference for the subject.

Typically the method includes, in the processing system:
  a) comparing first and second impedance values; and,
  b) determining the presence, absence or degree of a biological anomaly using the results of the comparison.

Typically the impedance values are at least one of:
a) measured impedance values; and,
b) impedance parameter values derived from measured impedance values.

Typically the impedance parameter values include at least one of:
a) an impedance at infinite applied frequency ($R_\infty$);
b) an impedance at zero applied frequency ($R_0$); and,
c) an impedance at a characteristic frequency ($Z_c$).

Typically the method includes, in the processing system, determining the impedance parameter values at least in part using the equation:

$$Z = R_\infty + \frac{R_0 - R_\infty}{1 + (j\omega\tau)^{(1-\alpha)}}$$

where: $R_\infty$=impedance at infinite applied frequency;
$R_0$=impedance at zero applied frequency;
$\omega$=angular frequency;
$\tau$ is the time constant of a capacitive circuit modelling the subject response; and,
$\alpha$ has a value between 0 and 1.

Typically the method includes, in the processing system:
a) causing at least one first impedance value to be measured at a site using a first electrode configuration; and,
b) causing at least one second impedance value to be measured at the site using a second electrode configuration.

Typically the processing system forms part of a measuring device for performing impedance measurements.

Typically the anomaly includes any one or a combination of:
a) a tissue anomaly; and,
b) an erroneous measurement.

Typically the tissue anomaly is a tissue lesion.

Typically the impedance measurements are performed using apparatus including an electrode array having a number of electrodes provided thereon, and wherein the method includes, in the processing system, causing impedance measurements to be performed using different ones of the electrodes in the array.

Typically the method includes:
a) causing a first measurement to be performed at a site using first and second electrodes as drive electrodes and using third and fourth electrodes as measurement electrodes; and,
b) causing a second measurement to be performed at the site using first and third electrodes as drive electrodes and using second and fourth electrodes as measurement electrodes.

Typically the method includes:
a) causing a measurement to be performed at a site using first and second electrodes as drive electrodes and using third and fourth electrodes as measurement electrodes; and,
b) causing a measurement to be performed at a second site using at least two of the first, second, third and fourth electrodes.

Typically the method includes:
a) causing a first measurement to be performed at a first site using first and second electrodes as drive electrodes and using third and fourth electrodes as measurement electrodes;
b) causing a second measurement to be performed at the first site using first and third electrodes as drive electrodes and using second and fourth electrodes as measurement electrodes;
c) causing a first measurement to be performed at a second site using third and fifth electrodes as drive electrodes and using fourth and sixth electrodes as measurement electrodes; and,
d) causing a second measurement to be performed at the second site using third and fourth electrodes as drive electrodes and using fifth and sixth electrodes as measurement electrodes.

Typically the apparatus includes a signal generator for generating drive signals, a sensor for sensing measured signals, and a multiplexer, and wherein the method includes, in the processing system selectively interconnecting the signal generator and the sensor to electrodes in the array using the multiplexer.

In a sixth broad form, the present invention seeks to provide apparatus for use in performing impedance measurements on a subject, the apparatus including a processing system that:
a) determines at least one first impedance value, measured at a site using a first electrode configuration;
b) determines at least one second impedance value, measured at the site using a second electrode configuration; and,
c) determines an indicator indicative of the presence, absence or degree of an anomaly using the first and second impedance values, the indicator being used in the detection of cervical cancer.

It will be appreciated that the broad forms of the invention may be used individually or in combination, and may be used for diagnosis of the presence, absence or degree of a range of conditions and illnesses, including, but not limited to the detection of lesions, tumours, or the like, as well as to allow impedance mapping to be performed more accurately by accounting for erroneous readings.

The detection of lesions can be used both in cancer screening, as well as in the triage of abnormal cytology or a HPV high risk genotype positive result.

BRIEF DESCRIPTION OF THE DRAWINGS

An example of the present invention will now be described with reference to the accompanying drawings, in which:

FIGS. 6A to 6D are schematic diagrams of example tetrapolar electrode configurations;

FIG. 7 is a schematic diagram of an example of a region of red blood cells introduced to a plasma to show visible diffusion;

DETAILED DESCRIPTION OF THE PREFERRED EMBODIMENTS

Figure 1A:
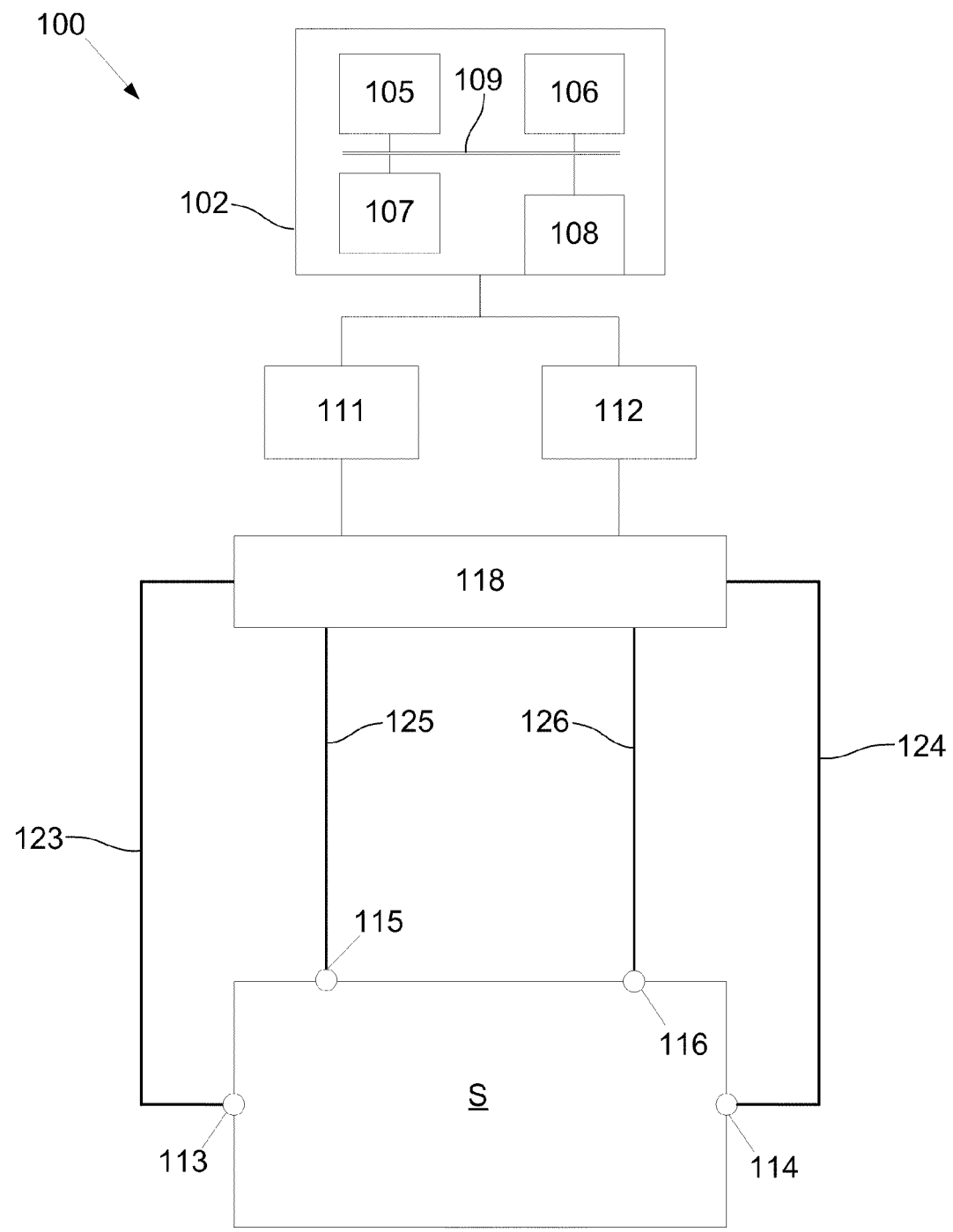
FIG. 1A is a schematic of an example of impedance measuring apparatus.

An example of apparatus suitable for performing an analysis of a subject's bioelectric impedance will now be described with reference to FIG. 1A.

As shown the apparatus includes a measuring device 100 including a processing system 102 coupled to a signal generator 111 and a sensor 112. In use the signal generator 111 and the sensor 112 are coupled to first electrodes 113, 114, and second electrodes 115, 116, provided on a subject S, via respective first leads 123, 124, and second leads 125, 126.

The connection may be via a switching device 118, such as a multiplexer, allowing the leads 123, 124, 125, 126 to be selectively interconnected to signal generator 111 and the sensor 112, although this is not essential, and connections may be made directly between the signal generator 111, the sensor 112 and the electrodes 113, 114, 115, 116.

Although only a single signal generator 111 and a single sensor 112 are shown in this example, this is not essential, and instead two signal generators 111 and two sensors 112 may be used, with each signal generator and each sensor being coupled to a respective one of the electrodes 113, 114, 115, 116 in use.

The processing system 102 typically includes a processor 105, a memory 106, an input/output device 107 such as a keyboard and display, and an external interface 108 coupled together via a bus 109, as shown. The external interface 108 can be used to allow the processing system 102 to be coupled to the signal generator 111 and the sensor 112, as well as to allow connection to one or more peripheral devices (not shown), such as an external database, or the like.

In use, the processing system 102 is adapted to generate control signals, which cause the signal generator 111 to generate one or more alternating drive signals, such as voltage or current signals, which can be applied to a subject S, via two of the electrodes 113, 114, 115, 116 (generally referred to as "drive" electrodes). The sensor 112 then determines measured signals representing the induced voltage across or current through the subject S, using the other two of the electrodes 113, 114, 115, 116 (generally referred to as "measurement" electrodes) and transfers appropriate signals to the processing system 102.

Accordingly, it will be appreciated that the processing system 102 may be any form of processing system which is suitable for generating appropriate control signals and interpreting an indication of the measured signals to thereby determine the subject's bioelectrical impedance, and optionally determine other information such as the presence, absence or degree of oedema, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like.

In one example, the processing system can be formed from first and second processing systems, such as a computer system and a processing system, such as an FPGA or the like. In this example, the computer system can be used to control the processing system, allowing the processing system to perform the measurement procedure, and allowing the computer system to be used to analyse the impedance measurements and displayed determined results. In a further example, the processing system can be incorporated into a measuring device, such as a probe, with the computer system being provided remotely to the measuring device.

The use of a separate computer system and processing system can lead to a number of benefits. For example, the processing system can be used to allow the custom hardware configuration to be adapted through the use of appropriate embedded software. This in turn allows a single measuring device to be used to perform a range of different types of analysis.

Secondly, this vastly reduces the processing requirements on the computer system. This in turn allows the computer system to be implemented using relatively straightforward hardware, whilst still allowing the measuring device to perform sufficient analysis to provide interpretation of the impedance. This can include for example displaying information such as relative fluid levels, body composition parameters, a "Wessel" plot, or other indicators, as well as using the impedance values to determine indicators, such as indicators indicative of the presence, absence or degree of anomalies such as lesions, or the like.

Thirdly, this allows the measuring device to be updated. Thus for example, if an improved measurement protocol is created, or an improved current sequence determined for a specific impedance measurement type, the measuring device can be updated by downloading new embedded software.

It will be appreciated however that this is not essential, and additionally, or alternatively, a single processing system may be used.

In use, the two electrodes 113, 114, 115, 116 that are to be used as drive electrodes are positioned on the subject to allow one or more signals to be injected into the subject S, with two other electrodes 113, 114, 115, 116 being positioned to act as measurement electrodes to allow signals induced within the subject, to be detected. The location of the electrodes will depend on the segment of the subject S under study, an example of which is shown in FIGS. 1B and 1C and further described below.

Once the electrodes are positioned, one or more alternating signals are applied to the subject S, via the drive electrodes. The nature of the alternating signal will vary depending on the nature of the measuring device and the subsequent analysis being performed.

For example, the system can use Bioimpedance Analysis (BIA) in which a single low frequency current is injected into the subject S, with the measured impedance being used directly in the identification of anomalies (which can include tissue anomalies, erroneous measurements, or the like), or performing impedance mapping.

In contrast Bioimpedance Spectroscopy (BIS) devices apply signals at a number of frequencies either simultaneously or sequentially. BIS devices typically utilise frequencies ranging from low frequencies (4 kHz) to higher frequencies (1000 kHz), and can use 256 or more different frequencies within this range, to allow multiple impedance measurements to be made within this range.

Thus, the measuring device 100 may either apply an alternating signal at a single frequency, at a plurality of frequencies simultaneously, or may apply a number of alternating signals at different frequencies sequentially, depending on the preferred implementation. The frequency or frequency range of the applied signals may also depend on the analysis being performed.

In one example, the applied signal is a frequency rich current signal from a current source clamped, or otherwise limited, so it does not exceed a maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between the measurement electrodes. The acquired signal and the measured signal will be a superposition of potentials generated by the human body, such as the ECG, and potentials generated by the applied current.

To assist accurate measurement of the impedance, buffer circuits may be placed in connectors that are used to connect the electrodes 113, 114, 115, 116 to the leads 123, 124, 125, 126. This helps eliminate contributions to the measured voltage due to the response of the leads 123, 124, 125, 126, and reduce signal losses.

A further option is for the voltage to be measured differentially, meaning that the sensor used to measure the potential at each measurement electrode only needs to measure half of the potential as compared to a single ended system. In one example, current can also be driven or sourced through the subject S differentially, which again greatly reduced the parasitic capacitances by halving the common-mode current.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analogue demodulation techniques will be known to persons skilled in the field.

In the case of BIS, impedance or admittance measurements can be determined from the signals at each frequency by comparing the recorded voltage and current signal. This allows demodulation to be used to produce an amplitude and phase signal at each frequency.

FIGS. 1B and 1C show an example of the apparatus for performing bioelectrical impedance implemented for use in cervical cancer detection. In this example, the measuring device is incorporated into a probe.

In one example, the probe 130 has a handle portion 132, which includes the processing system 102, signal generator 111, sensor 112, and switching device 118. An optional remote computer system 131 may be provided. The probe 130 has a probe portion 134 attached to the handle portion 132, where the probe portion 134 can include the leads and electrodes such as, for example, the leads 123 to 126 and a number of electrodes 150 that are selectively connectable to the signal generator 111 and the sensor 112, via the switching device 118, thereby allowing the electrodes 150 to selectively acts as the drive and sense electrodes 113, 114, 115, 116. It can be seen that in this example, nine electrodes are shown provided in a 3×3 array, but this is for the purpose of example only, and in practice any number of electrodes may be provided, as will be described in more detail below.

In use, the handle portion 132 of the probe 130 can be used to handle the probe 130, allowing the probe portion 134 to be inserted into or near the cervix, so that the electrodes 150 are positioned in contact with tissue of interest. The operator then activates a measurement procedure, causing the apparatus to perform impedance measurements on the tissue, with the results being analysed to allow any biological anomalies or lesions of the cervix, such as cervical cancer, to be detected.

Accordingly, the probe portion is typically made of a biologically inert material, such as a polymer based material such as polystyrene, polyethylene, polypropylene, acrylates, methacrylates, acrylics, polyacrylamides, and vinyl polymers such as vinyl chloride and polyvinyl fluoride, ie plastics, or the like. The probe is also typically shaped to conform to the shape of the vagina and cervix, to allow for easy and comfortable insertion into the subject.

It will be appreciated that either the probe portion 134, or the entire probe 130 can be disposable, such that the probe portion 134 is used once for a patient in order to minimise the risk of disease transfer between patients. Additionally, either the probe portion 134 or the entire probe 130 can be formed such that they are able to be sterilised. Thus, in one particular example, the probe portion 134 can be removably attached to the handle portion 132, so that after use, the probe portion 134 can be removed and disposed of. Alternatively, the probe portion 134 can include a cover or sterilised sheath which can be changed for each patient.

Typically, the probe portion 134 is separable from the handle portion 132, allowing the probe portion 134 to be replaced for each subject being tested, however this is not essential and a single bodied probe could be used. However, by providing separate probe and handle portions 134, 132, this allows the probe portion 134 to contain only the electrodes and leads, and not any of the associated electronics. This allows the probe portion 134 to be constructed cheaply and easily, allowing this to be formed from a disposable unit. In contrast, the handle portion 132, includes processing electronics required to generate and analyse the electrical signals, and hence this part of the device will be more expensive, and is therefore typically designed for reuse. In a further example, the probe portion 134 can include basic electronics, such as capacitive cancelling circuits, although these may also be incorporated into the handle portion 132.

Figure 1B:
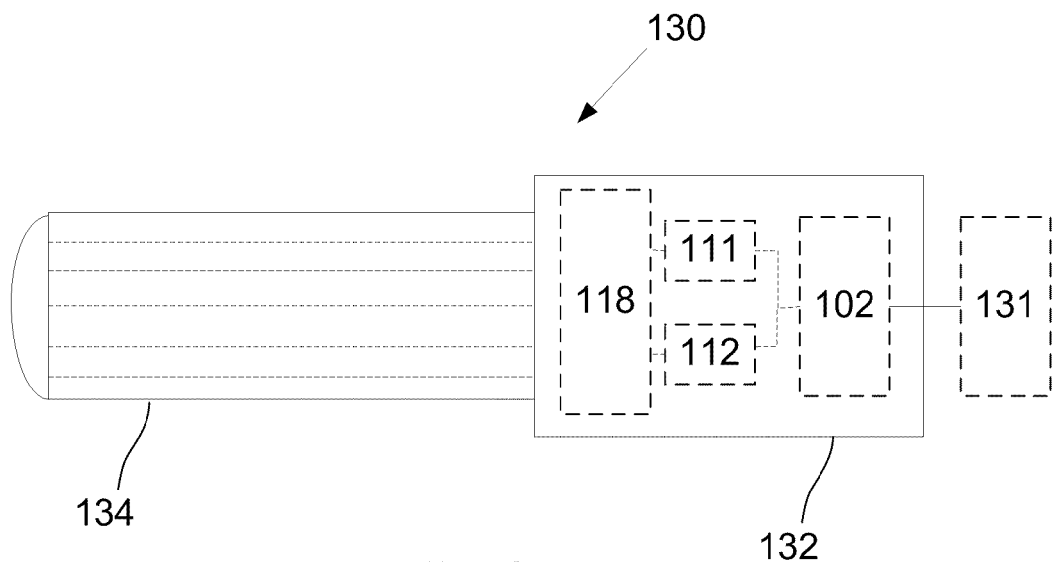
FIG. 1B is a schematic diagram of a side view of an example impedance measuring apparatus for use in cervical cancer detection.
Figure 1C:
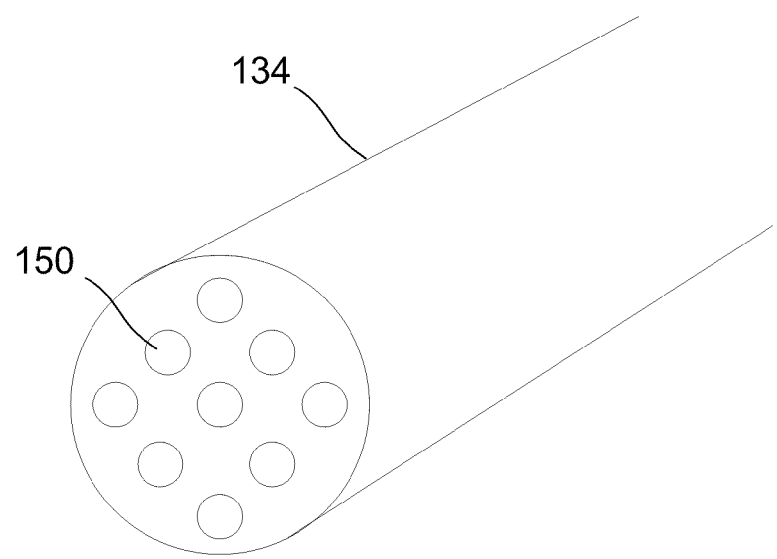
FIG. 1C is a schematic diagram of a front perspective view of the apparatus of FIG. 1B.
Figure 1D:
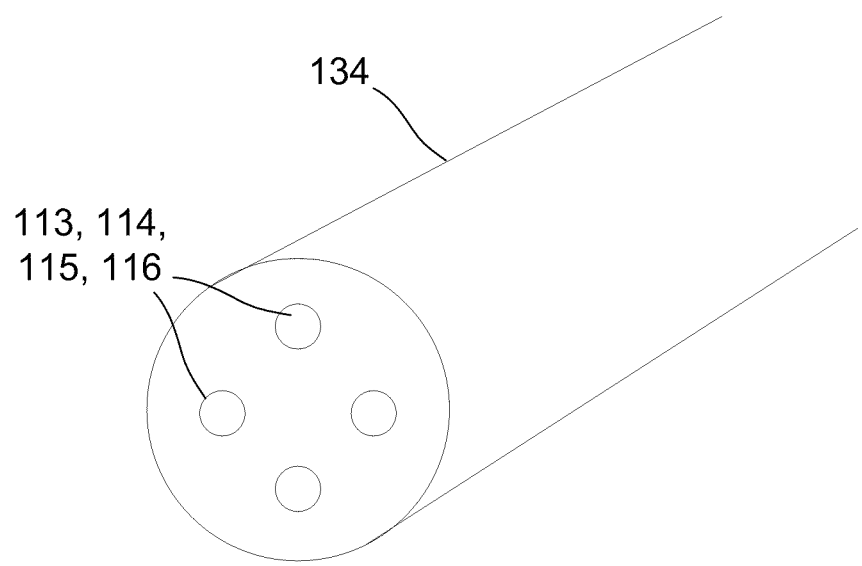
FIG. 1D is a schematic diagram of a second example of an impedance measuring apparatus for use in cervical cancer detection.
Figure 1E:
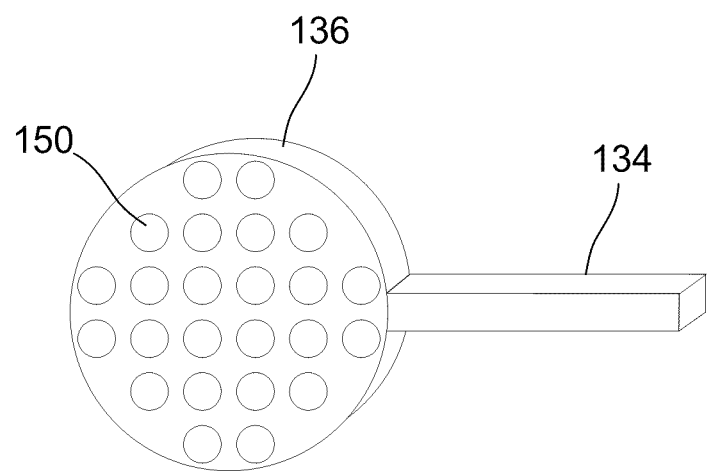
FIG. 1E is a schematic diagram of a second example of an impedance measuring apparatus for use in cervical cancer detection.

Alternative designs of probe portion 134 are shown in FIGS. 1D and 1E. In the example of FIG. 1D, the probe portion includes only four electrodes, which selectively act as the drive and sense electrodes 113, 114, 115, 116. It will be appreciated that four electrodes is the minimum needed to perform the impedance measuring process outlined in more detail below. Accordingly, in the event that only four electrodes are provided, then this requires that the apparatus is repositioned each time a different tissue site is to be analysed. However, by providing a larger array of electrodes 150, this can allow multiple tissue sites to be analysed without requiring movement of the probe portion 134. This can significantly reduce discomfort for the subject.

In the event that multiple electrodes are provided in an array, the number of electrodes can be limited by the diameter of the probe portion 134. Accordingly, in an alternative example, the probe portion can include a head 136, which includes the electrodes 150 mounted thereon. The head 136 is in the form of a plate having the electrodes 150 mounted on one side thereof. In use, this allows the head to be inserted into the cervix and gently pressed against the side walls of the cervix, thereby allowing each of the electrodes 150 in the array to contact the cervical tissue. This in turn increases the number of electrodes 150 that can be brought into contact with the cervical tissue at any one time, allowing measurements to be performed at multiple sites, and in multiple configurations, without requiring adjustment of the probe position, and whilst maintaining a minimum physical volume for the probe portion 134. This in turn reduces discomfort for the subject.

Figure 2:
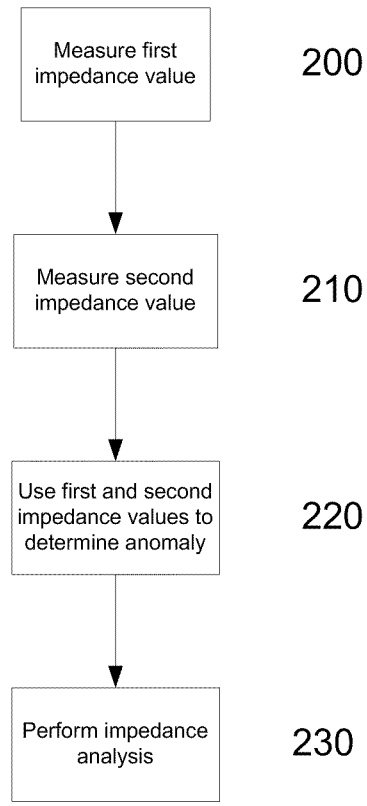
FIG. 2 is a flowchart of an example of a process for performing impedance measurements.

An example of the operation of the apparatus to detect anomalies when performing impedance mapping or other impedance measurements will now be described with reference to FIG. 2.

At step 200 a first impedance value is measured at a given site (such as for example, within the cervix). The impedance value is typically measured using a first electrode configuration, and whilst any form of electrode configuration may be used, this is typically a tetrapolar electrode configuration utilised to allow impedance readings to be measured at the specific site.

At step 210 a second impedance value is measured at the (same) site. This is typically achieved utilising an alternative electrode configuration and in particular, a configuration which is a modified version of the first configuration.

In this regard, the configuration typically utilises the same electrode placements on the subject, but applies the signals to and measures signals from different ones of the electrodes. Thus, for example, in a tetrapolar electrode configuration, the first measurement may be made by applying a current across first electrodes and measuring a voltage across second electrodes, whereas the second measurement may be made by applying the current across the second electrodes and measuring the induced voltage across first electrodes.

Typically, the preferred measurement option for a given site involves using first electrodes as the drive electrodes and second electrodes as the sense electrodes, for a first measurement. A second measurement is performed with one of the first and second electrodes acting as the drive electrodes, and with the other ones of the first and second electrodes acting as the sense electrodes, as will be described in more detail below.

At step 220 an indicator indicative of the presence, absence or degree of an anomaly using the first and second impedance values is determined. Thus, the indicator indicates if the measurement made at the site is erroneous or otherwise indicative of an anomaly. In particular, such a reading will typically arise if a low impedance lesion or other biological anomaly is present between a drive and a measurement electrode pair.

The indicator or anomaly can then be taken into account when performing analysis of impedance measurements at step 230. For example, the indicator may be used to identify and/or subsequently monitor the development of a low impedance lesion. Thus, this technique can be used to detect the presence, absence or degree of lesions or other biological anomalies. This can be used, for example, to identify cervical cancer, or the like. Additionally, and/or alternatively, knowledge of the anomaly can be taken into account when performing analysis of impedance measurements.

In one example, impedance measurements can be performed over a region, such as an area of a subject's skin, to allow impedance mapping or other similar analysis to be performed. As the presence of anomalies or other erroneous readings can have a negative impact on any such impedance mapping process, identification of these anomalies or erroneous readings allows readings at the corresponding site to be rejected or otherwise modified so that they do not adversely affect the impedance mapping process.

Figure 3:
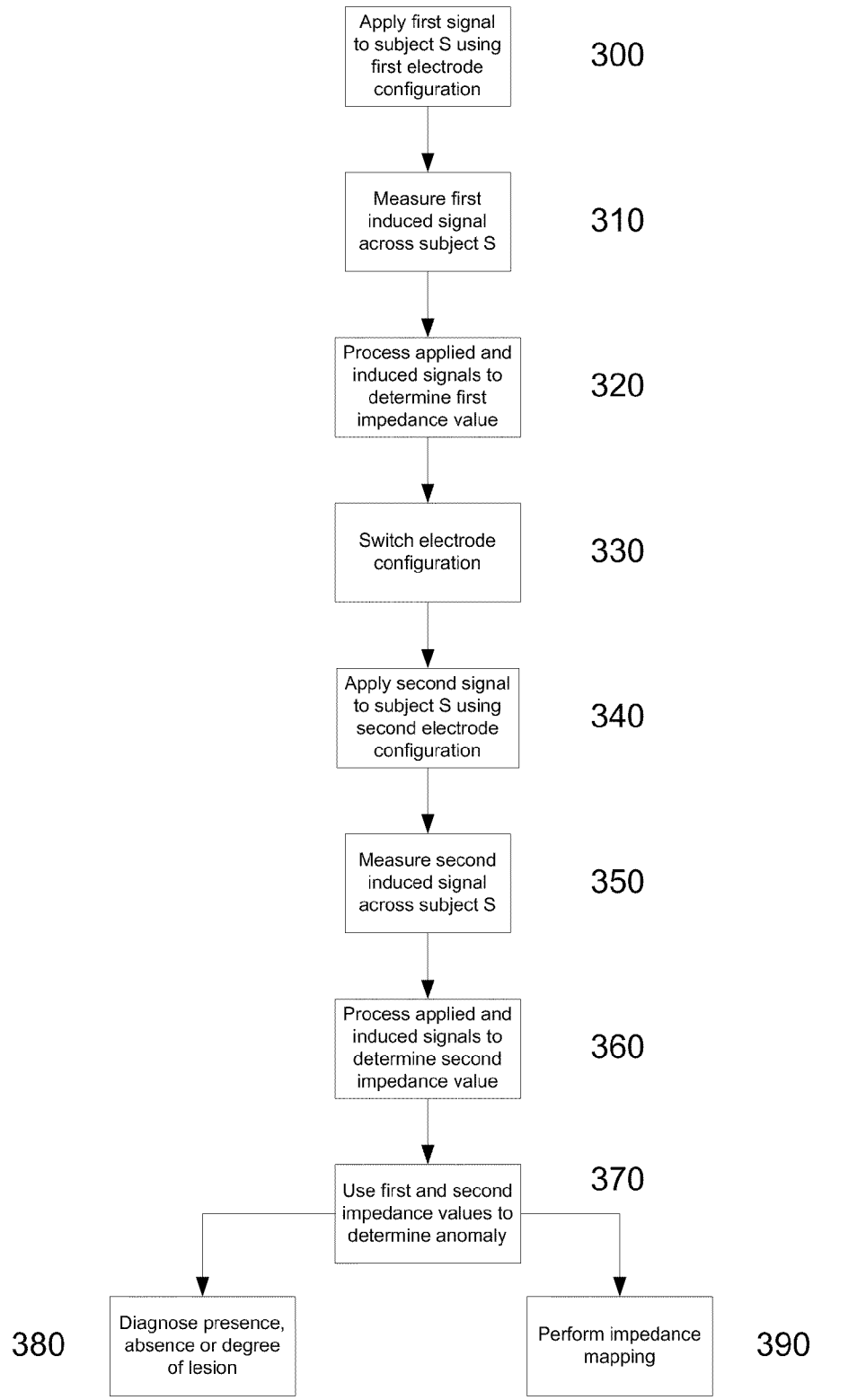
FIG. 3 is a flowchart of a second example of a process for performing impedance measurements.

An example of the process for identifying anomalies, including but not limited to tissue anomalies, erroneous readings, or the like will now be described in more detail with respect to FIG. 3.

In particular, at step 300 the signal generator 111 is used to apply a first drive signal to the subject S using a first electrode configuration. Thus for example, the current source 111 may be connected to the leads 123, 124, via the switching device 118, so that the electrodes 113, 114 act as the drive electrodes.

At step 310 a first signal induced across the subject S is measured. This is typically achieved by utilising the switching device 118 to interconnect the remaining measurement electrodes, in this case the electrodes 115, 116, to the sensor 112, thereby allowing signals induced within the subject S to be detected.

At step 320 the processing system 102 utilises an indication of the applied and induced signals to determine a first impedance value. The first impedance value may be formed from one or more measured impedance values. Thus, for example, if a single frequency BIA device is used, a single measured impedance value may be determined, whereas if a BIS device is used, multiple measured values may be determined, with a single value being determined for each applied frequency.

In addition, or alternatively to the impedance values being actual measured values, the impedance values may be based on impedance parameter values derived from the actual measurements. This can include parameter values such as the impedance at zero, characteristic or infinite frequencies ($R_0$, $Z_c$, $R_\infty$), as will be described in more detail below.

At step 330 the processing system 102 controls the switching device 118 to switch to an alternative electrode configuration. In this instance, for example, the electrodes 113, 115 may be used as the drive electrodes with the electrodes 114, 116 being used as measurement or sense electrodes. Any other alternative configuration may also be used, depending on the implementation.

At step 340, a second signal is applied to the subject S using the second electrode configuration, with the induced signal across subject S being measured at step 350. At step 360 the applied and induced signals are processed to determine a second impedance value, which again can be formed from one or more measured impedance values, or parameter values derived therefrom.

At step 370, the processing system 102 uses the first and second impedance values to determine if any tissue anomalies might exist. An erroneous measurement will typically be determined if the difference between the first and second impedance values is greater than a reference amount. The magnitude of this reference may vary depending upon a number of factors and the processing system 102 is therefore typically arranged to compare the difference between the first and second impedance values to a reference value, which can be stored in memory, or the like. The reference value could be previously determined for example based on sample data colleted for a nominal reference population, or based on the difference determined for other sites, as will be described in more detail below.

Once detected, this information can be used in one of two ways. For example, the measured values can be used to derive an indicator indicative of a biological anomaly, such as the presence, absence or degree of any tissue lesion, tumour, or the like, at step 380. The indicator can be in any one of a number of forms.

In one example, the indicator can be in the form of a numerical value or graphical representation thereof. The numerical value can be calculated, for example by comparing the difference between the first and second impedance values to a reference obtained from a normal population, or the like. Alternatively, the difference can be scaled relative to the reference. As a further alternative, the difference can be compared to a previously determined difference for the subject, allowing a longitudinal analysis to be performed. This allows variations in the difference over time to be monitored, which can in turn be indicative of the growth or reduction of the lesion. The indicator may also include thresholds, indicative of the presence, absence of lesions or other anomalies.

Alternatively, at step 390, the erroneous measurement can be taken into account when performing other impedance analysis. Thus, for example, if wound or other impedance mapping is being performed to monitor wound healing, or to perform large scale mapping of tissues, such as cervical tissue, or the like, any erroneous reading can be rejected to ensure that this does not overtly influence the outcome of the analysis. Examples of this will be described in more detail below.

Figure 4:
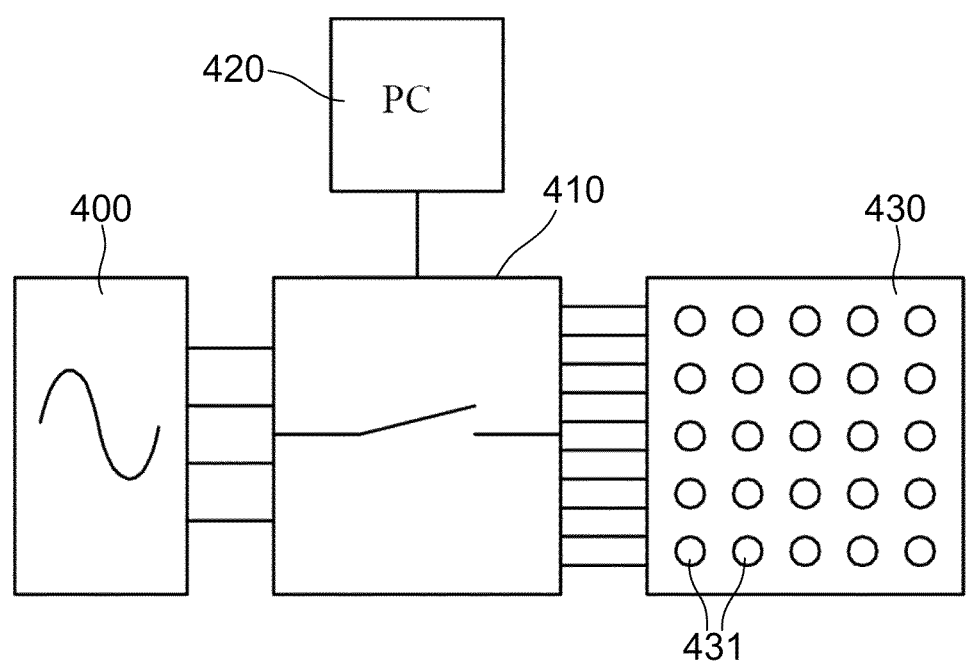
FIG. 4 is a schematic of a specific example of impedance measuring apparatus.

An example of a specific apparatus arrangement for performing impedance measurements, and in particular, for performing impedance mapping, will now be described with reference to FIG. 4.

In particular in this instance an impedance measuring device 400 is connected to a switching device in the form of a multiplexer 410, which is controlled by a processing system or computer system 420, such as a personal computer or the like. In this instance the multiplexer 410 is coupled to an electrode array 430 having a number of electrodes 431 provided thereon.

In use the measuring device 400 generates signals to be applied to the subject via the electrode array with these signals being coupled to respective ones of the electrodes 431 utilising the multiplexer 410. Similarly, signals induced across the subject S can also be returned from electrodes 431 to the impedance measuring device 400 via the multiplexer 410. Overall operation of the multiplexer 410 can be controlled using the computer system 420, allowing this process to be substantially automated.

In one specific example, the measuring device 400 is in the form of an Impedimed Imp SFB7™. The drive and measurement electrodes from the SFB7 can be directed through a multiplexer 410, such as a 32 channel multiplexer (ADG732) from Analog Devices and switching of the multiplexer output channels can be controlled via custom software operating on a standard computer system 420.

In this example, the electrode array 430 includes twenty five, 1 mm diameter electrodes separated by 0.77 mm in a 5×5 square. This allows a total of 64 separate measurements to be taken at 16 different sites giving an impedance map of 49 $mm^2$ on the surface of a subject, which may be an individual, a test medium, or the like. As a result of this, only 25 of the available 32 multiplexer channels are required for this arrangement.

Figure 5A:
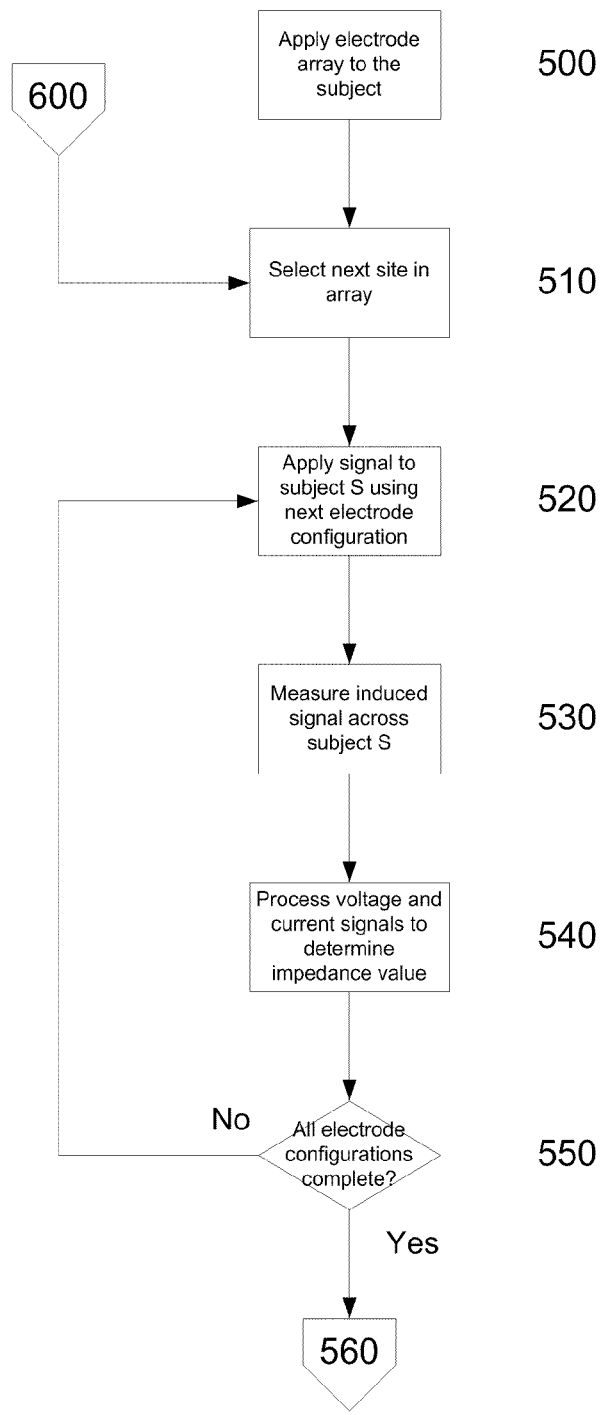
FIGS. 5A and 5B are a flowchart of an example of a process for performing impedance measurements using the apparatus of FIG. 4.
Figure 5B:
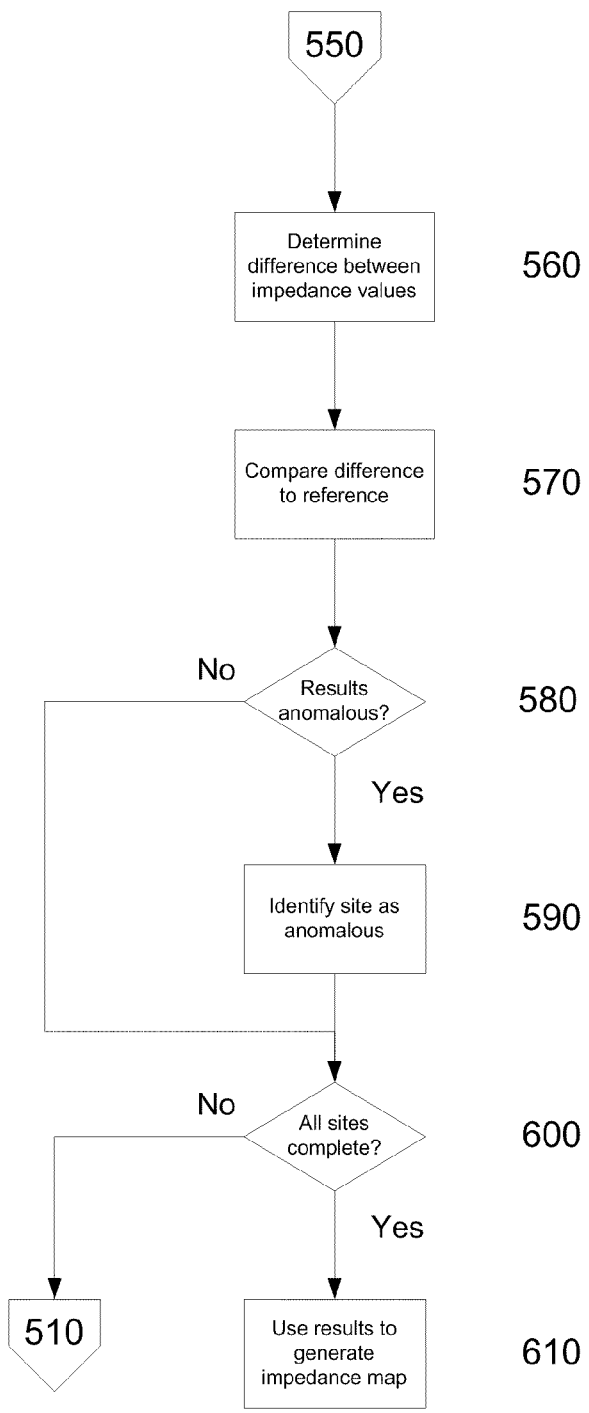
Figure 6E:
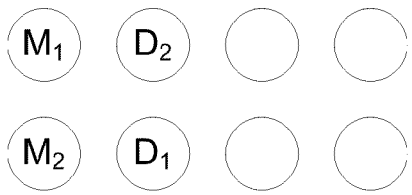
FIGS. 6E to 6J are schematic diagrams of an example of a sequence of electrode configurations used for performing measurements at multiple sites.
Figure 6F:
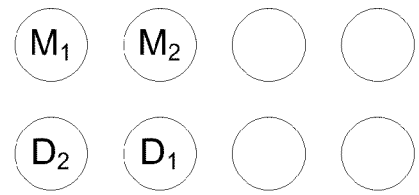
Figure 6G:
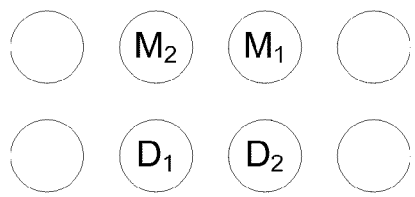
Figure 6H:
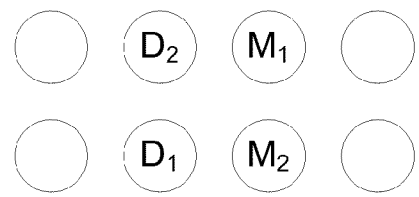
Figure 6I:
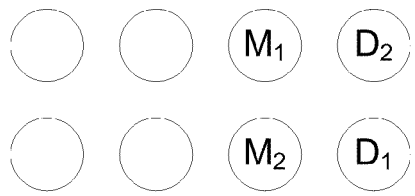
Figure 6J:
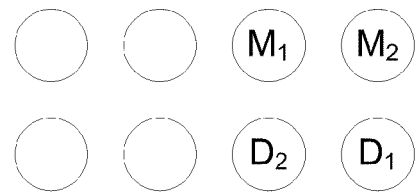

An example of use of the system will now be described with reference to FIG. 5.

At step 500 the electrode array 430 is applied to the subject S, and connected to the multiplexer 410, as described above. At this stage, systems, such as the measuring device 400, the multiplexer 410 and the computer system 420 are activated and configured as required in order to allow the measurement procedure to be performed.

At step 510 the computer system 420 selects a next site for measurement. The electrodes 431 are typically selected so as to form a tetrapolar arrangement, with a group of four electrodes 431 in the array 430 defining the site being measured. An example of this is shown in FIGS. 6A to 6D, in which four electrodes 431A, 431B, 431C, 431D are selectively used as measurement and drive electrodes for a single site.

In this example, four measurements can be made at each site by using the drive and measurement electrode arrangements shown in FIGS. 6A to 6D. Thus, in FIG. 6A, the electrodes 431A, 431B act as the measurement electrodes $M_1$, $M_2$, whereas the electrodes 431C, 431D act as the drive electrodes $D_1$, $D_2$. Successive measurements at the site can be made using different electrode configurations in which the drive and measurement electrodes $M_1$, $M_2$, $D_1$, $D_2$ are used as shown so that the tetrapolar configuration is effectively rotated by 90° for each successive measurement.

To achieve this, at step 520 the measuring device 400 controls the multiplexer 410 to couple the measuring device to the electrodes in accordance with a next one of the electrode configurations for the currently selected tetrapolar array. Thus, for example, for the first measurement, the arrangement shown in FIG. 6A can be used so that the electrodes 431A, 431B act as the measurement electrodes $M_1$, $M_2$, whereas the electrodes 431C, 431D act as the drive electrodes $D_1$, $D_2$.

The measuring device 400 then applies a drive signal to the subject via the selected drive electrodes 431C, 431D, allowing the signal induced across the measurement electrodes 431A, 431B to be measured at step 530. An indication of this measured signal is returned to the measuring device 400, to allow the measuring device 400 to process the voltage and current signals and determine one or more an impedance values.

The impedance values determined will depend on the preferred implementation. For example, in the event that the measuring device 400 is performing BIA, then typically a single impedance value is calculated representing the measured impedance.

In contrast, if the measuring device performs a multiple frequency BIS analysis, as is the case with the SFB7™ device described above, then the impedance value can be based on impedance parameter values, such as values of the impedance at zero, characteristic or infinite frequencies ($R_0$, $Z_c$, $R_\infty$), or an indicator indicative of the dispersion width of the impedance measurements ($\alpha$). These values can be derived by the measuring device 400 based on the impedance response of the subject, which at a first level can be modelled using equation (1), commonly referred to as the Cole model:

$$Z = R_\infty + \frac{R_0 - R_\infty}{1 + (j\omega\tau)} \quad (1)$$

where: $R_\infty$=impedance at infinite applied frequency,
$R_0$=impedance at zero applied frequency,
$\omega$=angular frequency,
$\tau$ is the time constant of a capacitive circuit modelling the subject response.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (2)$$

where: $\alpha$ has a value between 0 and 1 and can be thought of as an indicator of the deviation of a real system from the ideal model.

The value of the impedance parameters $R_0$ and $R_\infty$ may be determined in any one of a number of manners such as by:
solving simultaneous equations based on the impedance values determined at different frequencies;
using iterative mathematical techniques;
extrapolation from a "Wessel plot";
performing a function fitting technique, such as the use of a polynomial function.

It will be appreciated that as an alternative to the analysis being performed by the measuring device 400, the analysis can be performed in part, or in total, by the computer system 420, depending on the preferred implementation.

At step 550, the processing system 420 determines if all electrode configurations for the respective site are complete and if not returns to step 520. In this instance a next electrode configuration is selected, with steps 520 to 550 being repeated for this next electrode configuration. This process can then be repeated until each of the four electrode configurations shown in FIGS. 6A to 6D have been utilised for the current site.

Whilst it is possible to use all four of the indicated electrode configurations for the tetrapolar configuration, this is not essential, and in some circumstances, it is sufficient to use any two or more of the possible configurations. Thus, for example, the configurations used in FIGS. 6A and 6B can be used, in which the tetrapolar electrode configuration is effectively rotated by 90°. This is particularly useful as one drive and measurement electrode is effectively exchanged in the two different configurations, thereby maximising the chance of lesions located between the drive and measurement electrodes from being located, without requiring switching of each of the electrodes.

Furthermore, this arrangement can be used to provide a sequence of drive and measurement electrode configurations that can be used to perform multiple measurements at successive sites, with only a single drive and single measurement electrode being switched between successive measurements. An example of this is shown in FIGS. 6E to 6J.

Once all the electrode configurations are complete for a specific site, the measuring device 400 or the computer system 420 is used to analyse the impedance values and determine if the impedance measurements are indicative of a tissue anomaly. As mentioned above this may be achieved in any one of a number of ways but typically involves examining the difference between measured impedance values. The reason for this is that the impedance measured at a given site should be substantially invariant irrespective of the electrode configuration used. Consequently, any variation in measured impedance values for different electrode configurations indicates that the tissue is non-uniform and in particular that there is likely to be a low impedance lesion situated between the drive electrodes $D_1$, $D_2$ and the measurement electrodes $M_1$, $M_2$.

In this regard, when the electrodes are provided in the arrangement of FIGS. 6A to 6D, there are usually regions of positive sensitivity between the drive electrodes $D_1$, $D_2$ and between the measurement electrodes $M_1$, $M_2$. In addition to this, there are generally regions of negative sensitivity between each pair of drive and measurement electrodes $D_1$, $M_2$ and $M_1$, $D_2$. These size and magnitude of the areas of negative and positive sensitivity will vary depending on the exact electrode configuration.

For negative field region, a lower resistance than the surrounding tissue will result in an increase in measured impedance, whereas a lower resistance in the positive field region will result in a decrease in measured impedance. Example tissue electrical properties as given by Brown, B. H., Tidy, J. A., Boston, K., Blackett, A. D., Smallwood, R. H. and Sharp, F. (2000a). "*Relation between tissue structure and imposed electrical current flow in cervical neoplasia,*" The Lancet 355: 892-895, are shown in Table 1 below.

TABLE 1

| Healthy Tissue Mean (SD) | Cancerous Tissue Mean (SD) |
|---|---|
| $R_E$ = 19.0 (7.77) m | $R_E$ = 3.85 (2.89) m |
| $R_I$ = 2.31 (4.04) m | $R_I$ = 6.10 (2.57) m |
| C = 1.12 (1.96) µF/m | C = 1.01 (1.93) µF/m |

Thus, as cancerous tissue generally has a lower resistance, a cancerous lesion between the drive electrodes $D_1$, $D_2$ or between the measurement electrodes $M_1$, $M_2$ will result in a decreased impedance measurement, whereas a lesion between the each pair of drive and measurement electrodes $D_1$, $M_2$ or $M_1$, $D_2$, will result in an increased impedance measurement.

It will therefore be appreciated that examining differences between impedance measurements with different electrode configurations can allow tissue anomalies such as lesions, to be detected.

In one example this is achieved by determining the difference between the impedance values determined using the different electrode configurations, at step 560. The maximum determined difference is then compared to a reference at step 570. The reference, which is typically previously determined and stored in memory of the measuring device 400 or the computer system 420, represents a threshold value so that if the difference between impedance values is greater than the reference, then this indicates that a tissue anomaly is present.

The reference can be determined in any one of a number of ways depending on the preferred implementation. For example, the reference may be determined by studying a number of healthy individuals (individuals without lesions or other biological anomalies) and/or unhealthy individuals (individuals with lesions or other anomalies) and calculating a range of variations between impedance values at a given site. This can be used to provide an indication of typical differences between impedance values for a healthy individual, thereby allowing a threshold to be established for tissue anomalies.

A further alternative is to derive the reference from previous measurements made for the respective individual. For example, if the individual undergoes a medical intervention, such as surgery, or the like, which may result in a lesion forming, then measurements can be made for the individual prior to the intervention, or following initial development of the lesion. This can be used to establish a baseline of differences in impedance values for the individual, either prior to the lesion forming, or following lesion formation. This baseline can then be used as a subject specific reference so that changes in the difference between the impedance values for the individual, can be used to monitor lesion development and/or effectiveness of treatment.

A further option is to determine the reference using a statistical analysis of measurements made for a number of different sites. This could be performed by examining the mean difference for a number of sites over a region, and then calculating the reference based on a value that is a number of standard deviations from the mean. Accordingly, in this instance, an anomaly is identified if the difference for a site is more than a set number of standard deviations from the mean difference value for a number of sites.

In any event, if the reference is exceeded and the result is determined to be indicative of a tissue anomaly at step 580, then the site is identified as a tissue anomaly at step 590, in which case an appropriate indicator can be generated. The indicator could be indicative of the difference, the measured impedance values, impedance parameters, or the like. Alternatively, the indicator could be indicative of the result of the comparison, such as a colour indication indicating the presence or absence of a lesion, tumour or other anomaly. Thus, in one example, the probe can include indicator lights, allowing the indication to be provided. Alternatively, output may be via a display, or the like.

Once this is completed or otherwise, at step 600 the computer system 420 will determine if all sites are complete and if not will return to step 510 to select the next site in the electrode array 430. This will typically involve using the electrodes 631C, 631D and two electrodes in the next column in the array.

This process can be repeated for all of the sites defined by the electrode array 630, allowing an impedance map to be generated at 610. An indicator in the form of an impedance map can be used to indicate variations in tissue properties, or the like, which in turn can be used for a number of purposes, such as to monitor healing of wounds, or to allow anomalies to be identified, or the like.

As will be appreciated by persons skilled in the art, being able to identify, and subsequently discount or otherwise account for such tissue anomalies allows improved results to be obtained for impedance mapping processes.

Furthermore, this process can also be used to identify and monitor low impedance lesions, tumours or the like. For example, determining the magnitude of the difference between different impedance values obtained for a given site allows an indication of the severity of the lesion to be determined. By monitoring changes in the difference over time, this allows variations in lesion severity over time to be monitored.

Specific example trials of the process of performing impedance mapping will now be described.

The blood for each trial was collected from the same animal and treated with 70 mg/L of heparine to prevent coagulation. Blood for each measurement was prepared in the same manner by allowing it to cool to room temperature (22° C.) and the red blood cells separated via a centrifuge. The separated red blood cells and plasma could then be mixed in appropriate proportions to obtain the required haematocrit for testing. Samples were also collected and allowed to coagulate, these were used to represent a high impedance tissue medium at $R_0$ due to the small extracellular space.

In a first example, impedance maps were initially established for homogenous haematocrit in an in-vitro environment. To achieve this, bovine blood was used as the conductive medium, with impedance maps being obtained using homogenous samples with a range of haematocrit values (0, 20, 40, 60, 80%).

Figure 8:
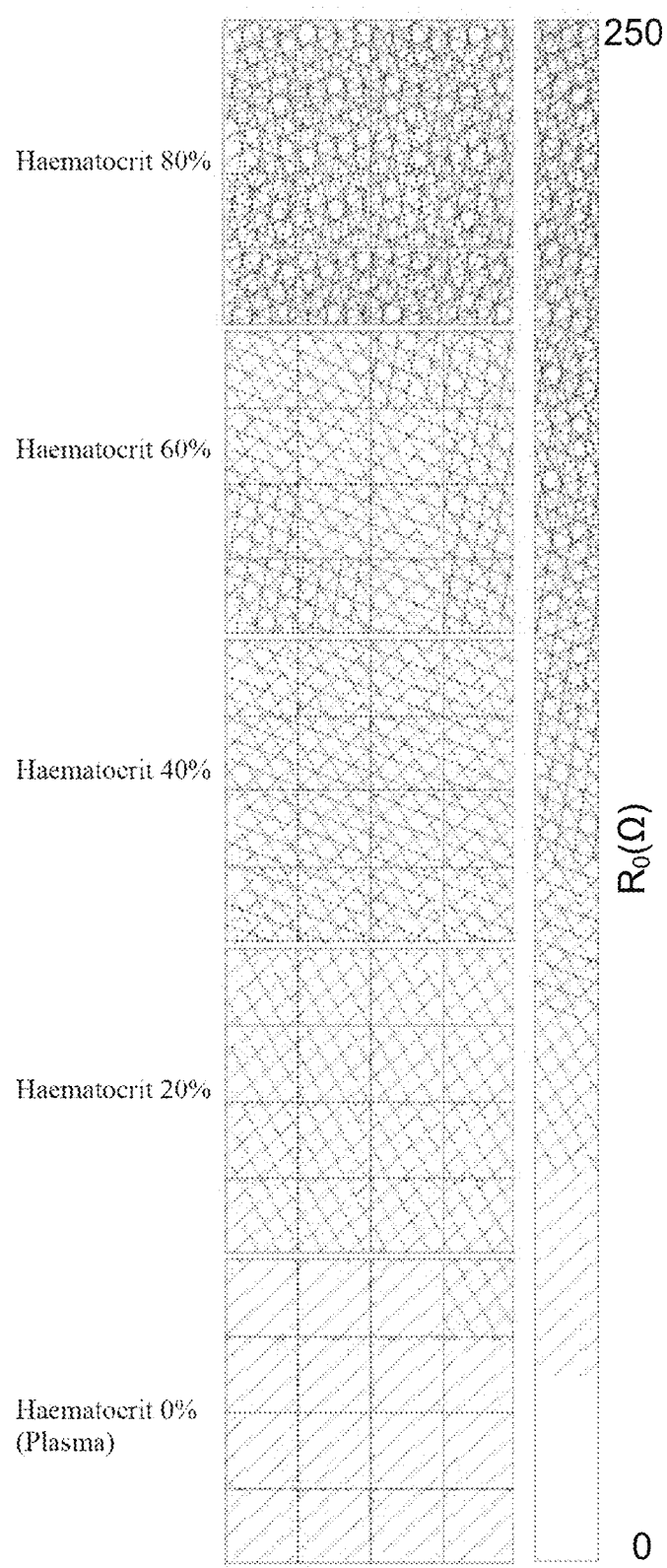
FIG. 8 is a schematic diagram of varying haematocrit value over an area of the electrode array of FIG. 4.
Figure 9A:
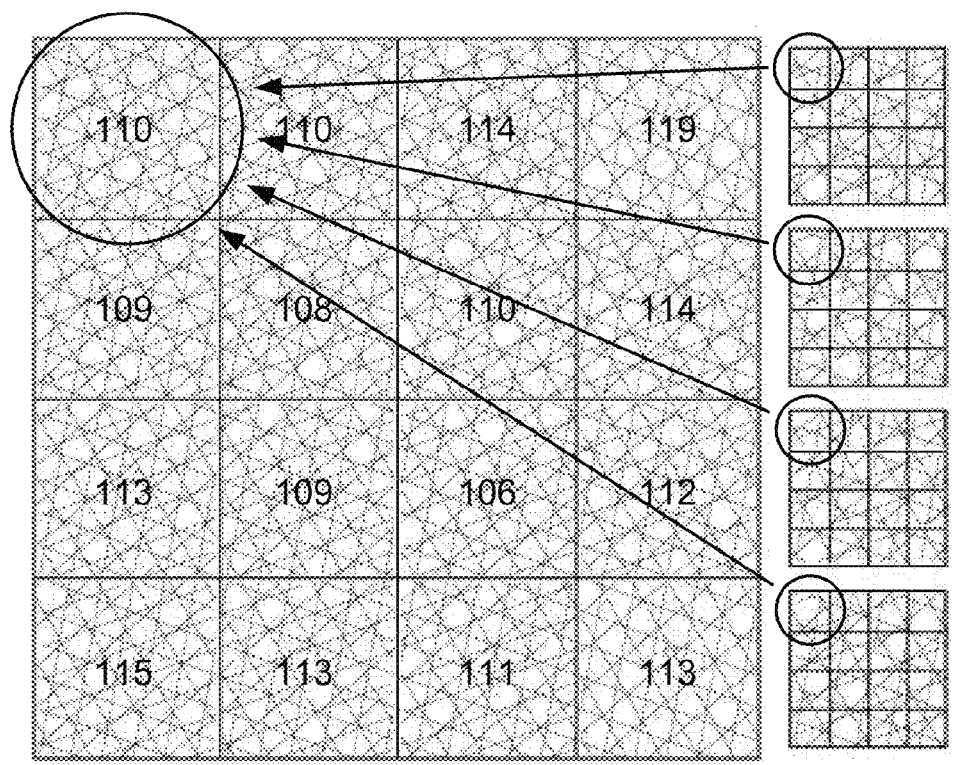
FIG. 9A is a schematic diagram of average $R_0$ maps for haematocrit of 60% and for the tetrapolar electrode arrangements of FIGS. 6A to 6D.

The impedance maps of $R_0$ measured for blood samples of various haematocrit are shown in FIG. 8. Each measurement location shown was measured using the tetrapolar electrode orientation arrangement described above, at each of the four possible electrode orientations. These four $R_0$ values measured using different electrode orientation were then averaged to produce one $R_0$ map as shown in FIG. 9A.

Figure 9B:
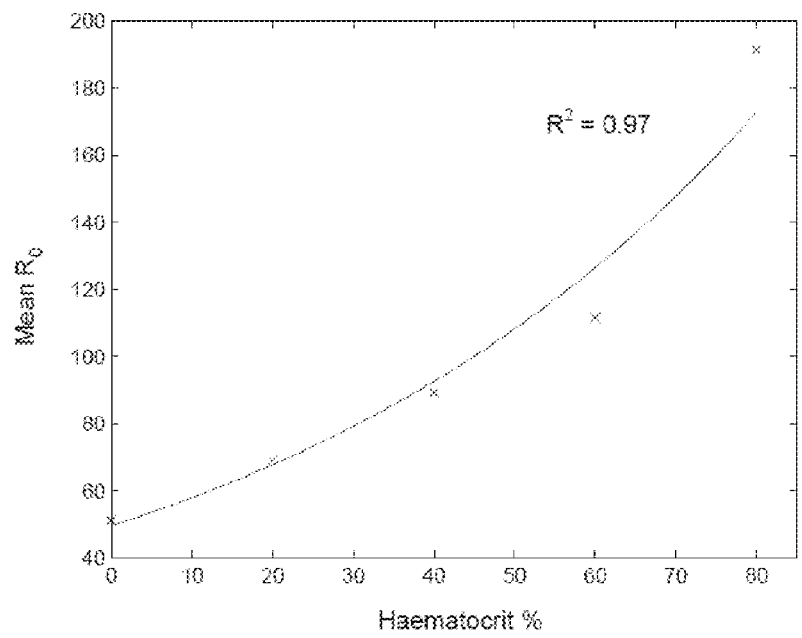
FIG. 9B is a plot of an example of a mean value of $R_0$ for each impedance map of FIG. 9A against haematocrit concentration.

A plot of mean $R_0$ for each impedance map against haematocrit is shown in FIG. 9B. This highlights that there is a large increase in impedance with haematocrit concentration. The plot follows an exponential trend as expected since the $R_0$ value of a sample with haematocrit of 100% would approach infinity due to the very small extracellular space. The range of haematocrit values has also shown to have a significant and measurable change in $R_0$. This is useful if impedance maps were to be determined with two or more volumes of blood with differing haematocrits.

In a second trial, the electrode array 430 was covered with plasma (haematocrit of 0%) and red blood cells (haematocrit of 100%) injected onto the corner of the electrode array, as shown for example in FIG. 7.

Figure 10:
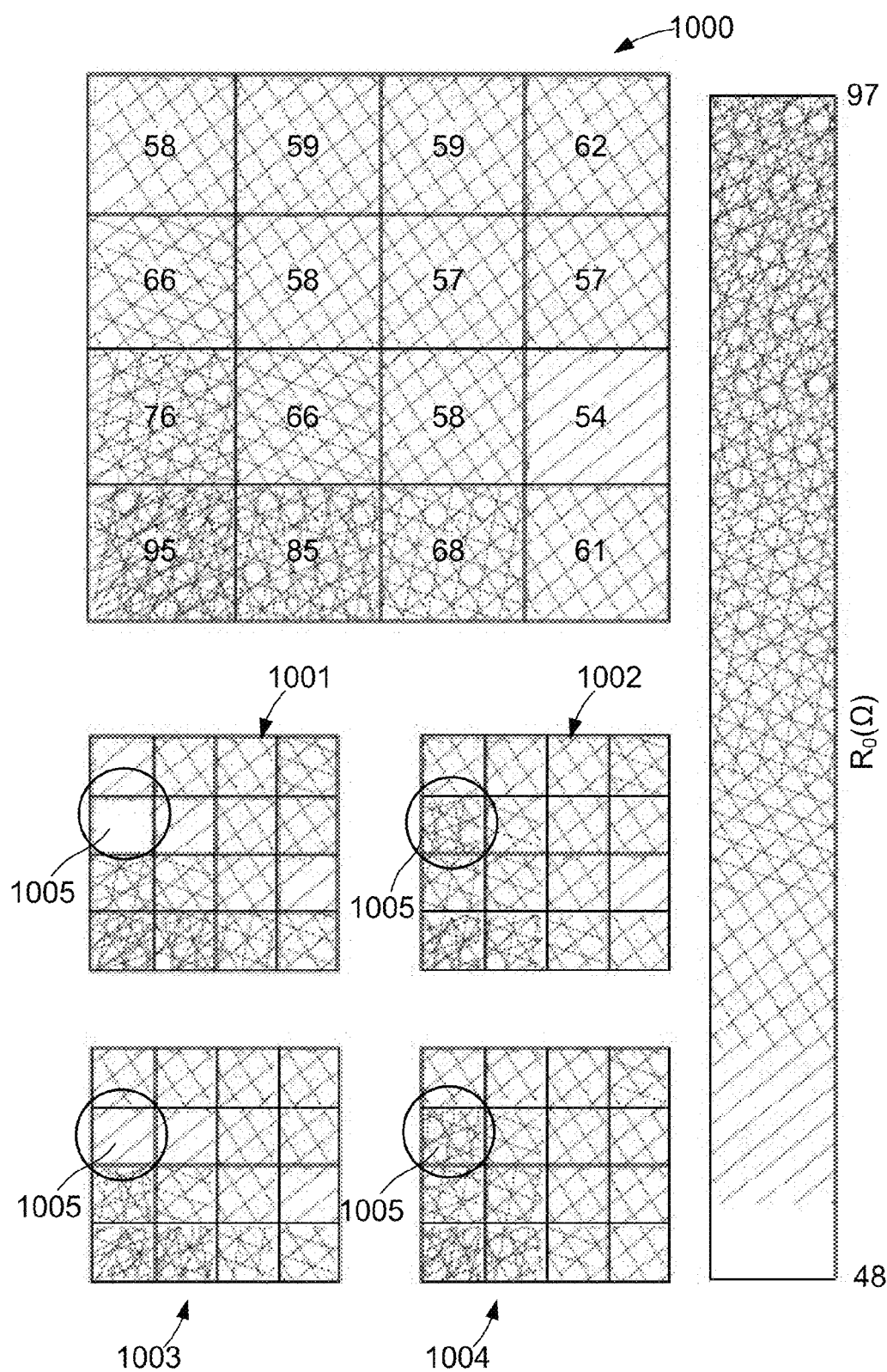
FIG. 10 is a schematic diagram of example impedance maps for plasma with introduced red blood cells in the lower left corner for the tetrapolar electrode arrangements of FIGS. 6A to 6D.

An example of the bioimpedance map of an average value of $R_0$ obtained for each site is shown at 1000 in FIG. 10. The smaller four maps 1001, 1002, 1003, 1004, correspond to the impedance values for $R_0$ measured using respective electrode configurations, as shown for example in FIGS. 6A to 6D.

It is evident from the above examples that bioimpedance maps for haematocrit 0 to 80% result in reasonably consistent values of $R_0$ (standard deviation<3%). The uniform measurements also demonstrate that the remaining 21 electrodes have little effect on the measurements from the 4 electrodes actively involved. Hence these 21 electrodes do not shunt the current between the active drive electrodes.

The bioimpedance map of plasma with introduced cells clearly shows an increase in $R_0$ at the site of the introduced cells, shown in FIG. 10. The $R_0$ value in the lower left corner (95Ω) is much higher than that in the upper right corner (62Ω) which corresponds to that of the homogenous plasma sample. While the resistance in the lower left corner is higher than that of plasma it is less than that obtain for 80 and 60% haematocrit. The reason for this is due to the cells dispersing throughout the plasma (as shown in FIG. 7) effectively reducing the haematocrit of the introduced red blood cell sample.

As shown in this example, the values of $R_0$ determined for the site 1005 differ significantly for the four different orientations, thereby indicating the presence of a biological anomaly at the site 1005.

In this example, the sensitivity region between the two electrodes 431B, 431D is positive for the maps 1002, 1004 resulting in an increased measured impedance if a higher impedance medium is present between the electrodes. This increase in impedance is clearly seen in the maps 1002, 1004. The maps 1001, 1003 on the left show a decrease in impedance because the region between the two electrodes 431B, 431D is of negative sensitivity in this configuration, thereby resulting in a decreased measured impedance when a higher impedance medium is located in the region.

When performing an impedance analysis, the can be taken into account by excluding this site from the larger impedance map, allowing an accurate average to be determined that excludes any anomaly. Alternatively different mechanisms may be used for taking this into account. For example, averaging of the four measured values of $R_0$, at the given site, can reduce the impact of the tissue anomaly. In this regard, the averaged impedance map would be unaffected since the higher and lower measured impedance values effectively average to cancel each other out, so that the $R_0$ value in this region of the larger map is not anomalous.

Alternatively, the impedance of adjacent sites can be used to determine a value for $R_0$ which is unaffected by the tissue anomaly. Thus, for example, examination of the maps 1001, 1002, 1003, 1004 for each tetrapolar configuration highlights that the determined impedance values determined for the site 1005 in the maps 1001, 1003 are similar to those of adjacent sites, whereas the impedance values determined for the site 1005 in the maps 1002, 1004 are significantly different. This implies that the lesion or other tissue anomaly is located between the drive and measurement electrodes for the electrode configurations used in determining the maps 1002, 1004, meaning that these readings are erroneous. Consequently, the impedance value used for the overall impedance map could be based on the impedance values determined for the impedance maps 1001, 1003 as these readings are more likely to be accurate.

This can be performed for example to discount readings that are believed to be anomalous, for example due to errors in the measuring process, poor electrode contact, or the like.

However, more typically the results are used to detect tissue anomalies, such as lesions or the like. Thus, as measurements made using orthogonal electrode orientations at a region of non-homogeneity will produce different measured impedances, whereas a region of homogeneity will produce the same measurements. This allows tissue anomalies, such as lesions, to be identified, and furthermore allows lesion boundaries to be determined.

Figure 11:
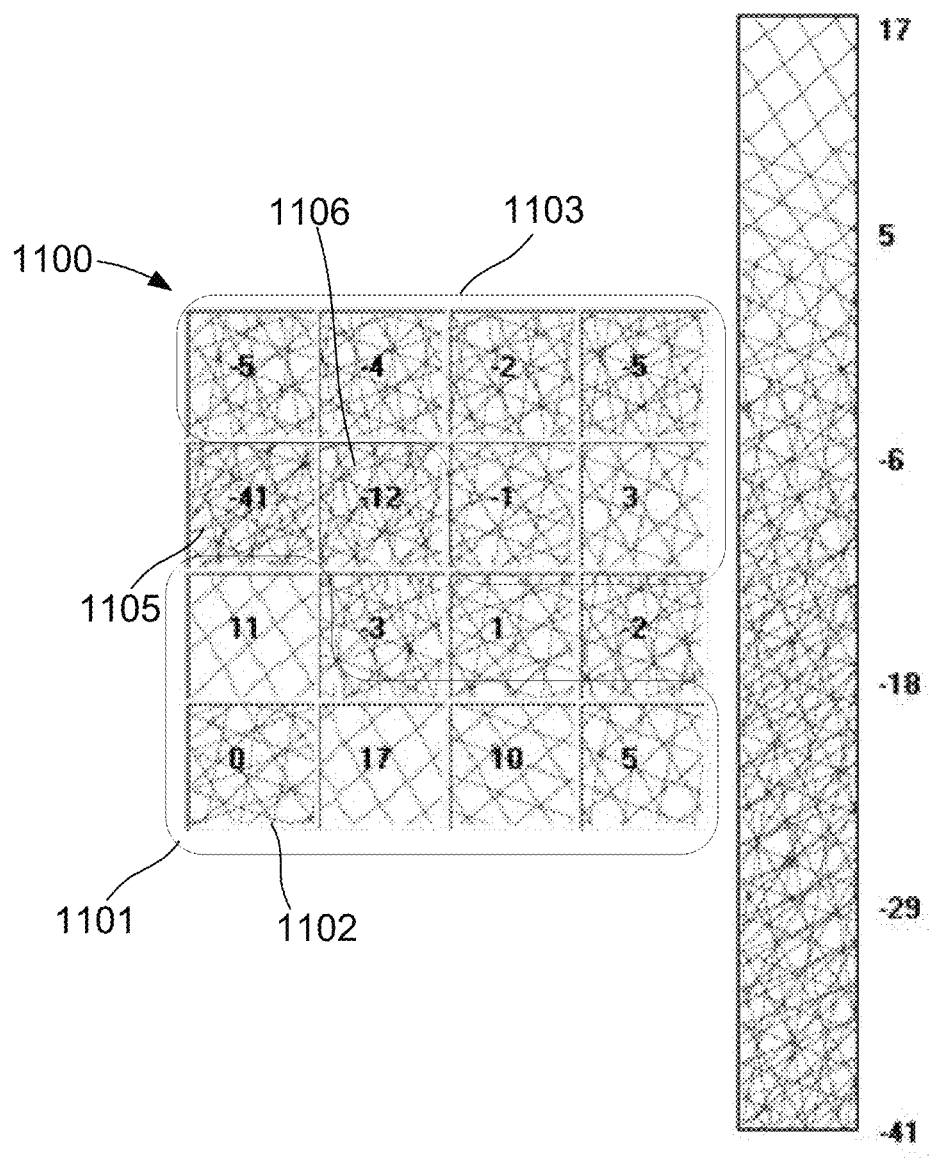
FIG. 11 is a schematic diagram of an example impedance difference map for use in identifying a tissue anomaly.

An example of this will now be described with reference to FIG. 11. For the purpose of this example, the impedance map of plasma with introduced red blood cells shown in FIG. 10 was used. In this example, the smaller maps 1001, 1003 are averaged, as are maps 1002, 1004, with the difference between these resulting maps being shown in the map 1100 of FIG. 11.

In this example, a region 1101 is highlighted which has low positive values of $R_0$, where dispersed blood is present, and this is due to different haematocrits being located under each of these electrode sets. Within this region, the site 1102 has an $R_0$ value of zero due to a high but homogeneous haematocrit sample being located under the electrode set.

In an upper right region 1103 of the impedance map, the average $R_0$ values are close to zero due to the sample under the electrode sets being homogeneous plasma, the red blood cells having not dispersed into this region.

At the site 1105, a large negative value of $R_0$ is present, implying the presence of a tissue anomaly or lesion. The site 1106 is also negative, but not to such a degree. This implies that a tissue anomaly is likely to be present at the site 1105 and that this may extend slightly into the site 1106. Accordingly, it will be appreciated that this not only allows tissue anomalies to be identified, but also allows the extent and/or boundaries of the tissue anomaly to be determined.

Figure 12A:
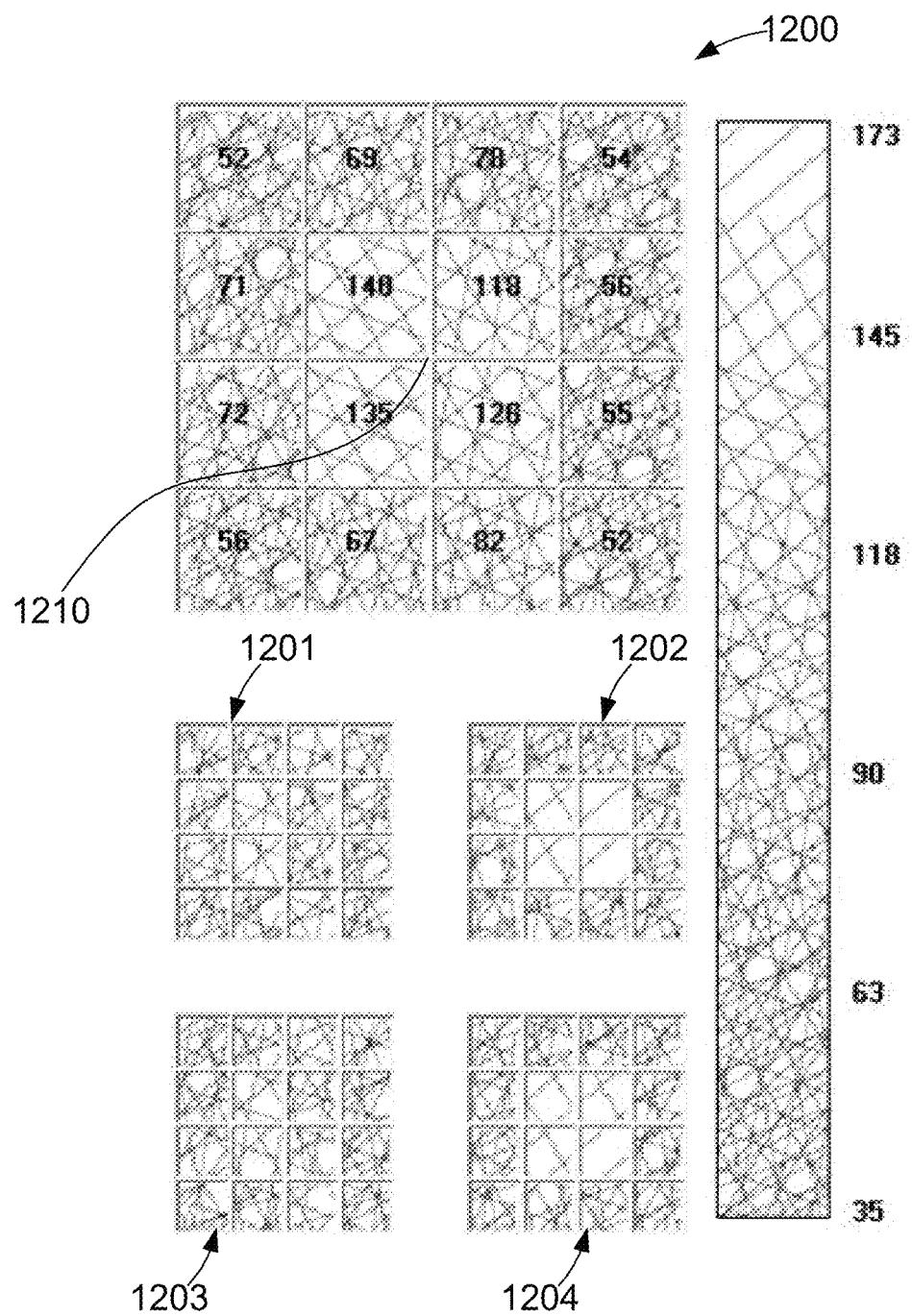
FIG. 12A is a schematic diagram of example impedance maps for plasma with an introduced red blood cell clot covering a central electrode.
Figure 12B:
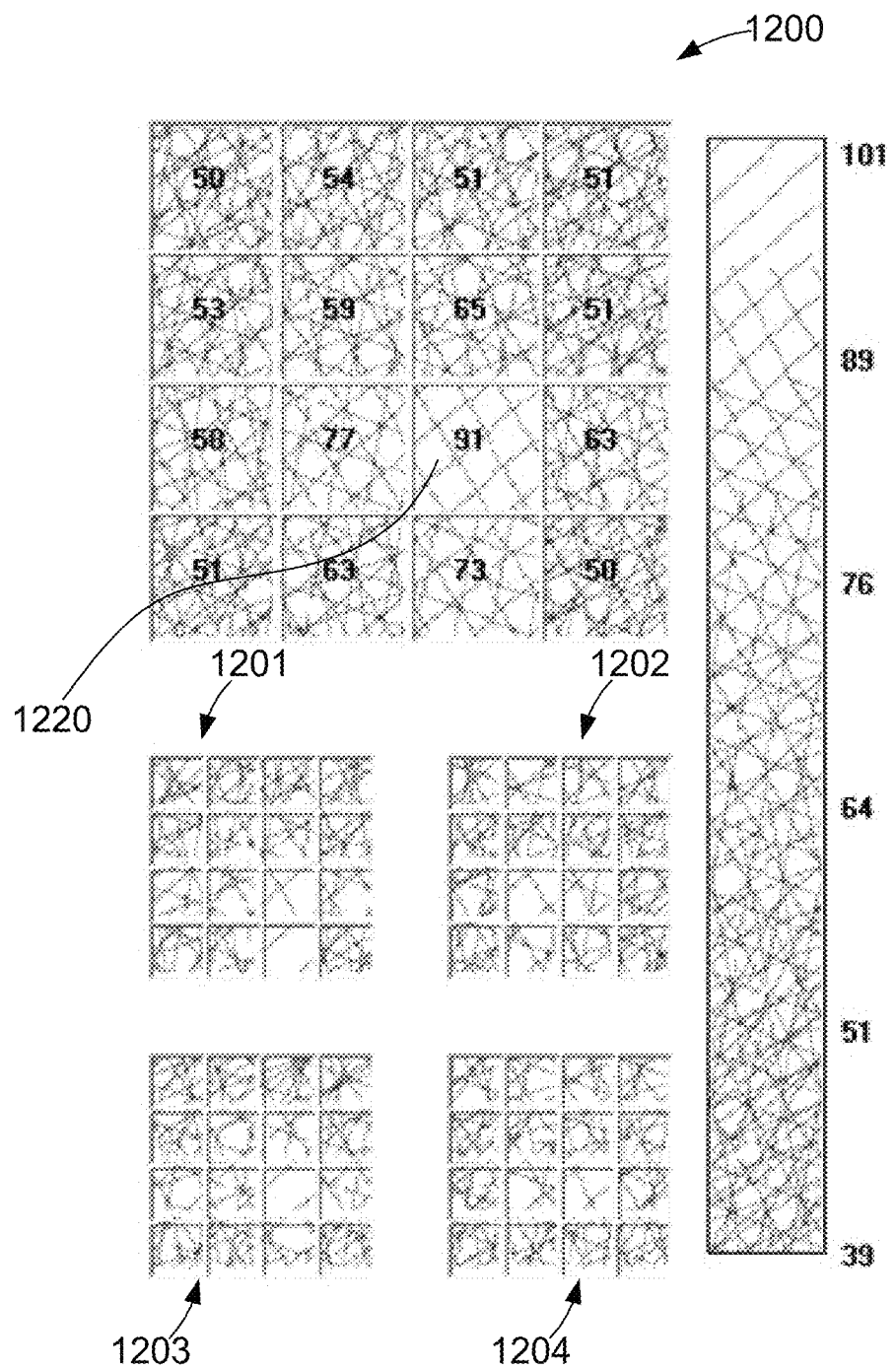
FIG. 12B is a schematic diagram of example impedance maps for plasma with an introduced red blood cell clot covering four electrodes associated with a respective measurement site.
Figure 12C:
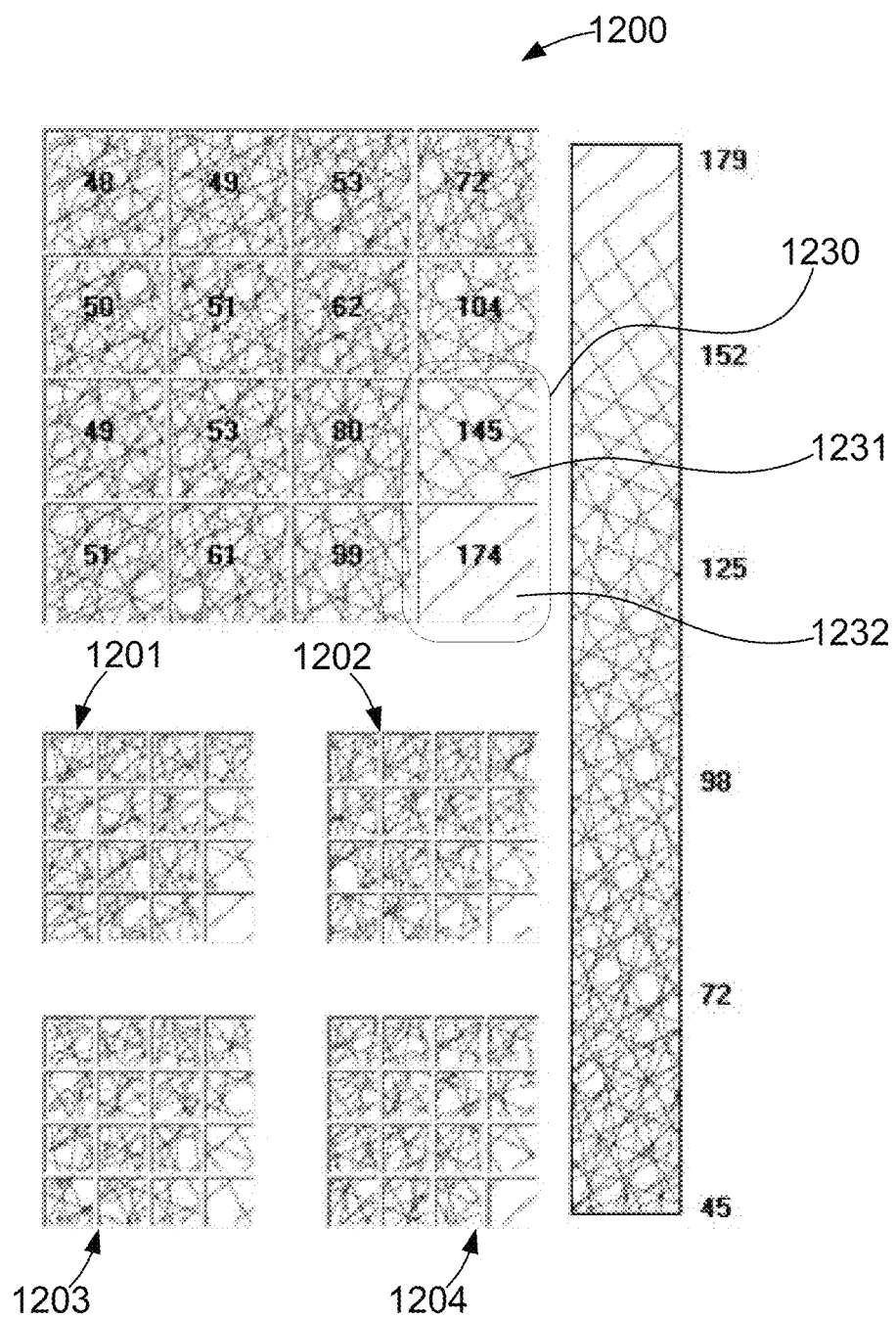
FIG. 12C is a schematic diagram of example impedance maps for plasma with an introduced red blood cell clot covering two measurement sites.

In a third example, a clot was introduced to the plasma in place of the red blood cells. FIGS. 12A, to 12C, display typical impedance maps 1200 with clots introduced in various regions on the electrode array. In the example of FIGS. 12A to 12C, the average value of $R_0$ obtained for each site is shown at 1200, with the four smaller maps 1201, 1202, 1203, 1204, corresponding to the impedance values for $R_0$ measured using respective electrode configurations, as shown for example in FIGS. 6A to 6D.

In FIG. 12A, the clot is introduced beneath a central electrode, the location of which is shown at 1210. In FIG. 12B, the clot is located at the site 1220, whilst in the example of FIG. 12C, the clot is provided in the region 1230, encompassing the sites 1231, 1232. These examples show clear impedance changes at the boundaries of the red blood cell clots due to minimal dispersion of red blood cells. This highlights how in practice the process can be used to identify the size of tissue anomalies, such as lesions and monitor their growth or change in shape over time.

It will therefore be appreciated that the above described methods provide techniques for identifying the presence, absence and even extent of tissue anomalies, such as lesions. These anomalies did not appear to alter the resultant impedance map once averaged, meaning that the averaging of results prevents the tissue anomalies being detected. However, this does mean that even in the event that anomalies exist, this avoids the need to remove and discard such measurements.

Thus, the above described techniques provide a non-subjective method for determining lesion size and hence possible biopsy margins.

Notably, by using an electrode array coupled to a suitable switching system, this allows measurements to be rapidly performed over an area of the subject. Furthermore, by using only two measurements at each site, this can reduce the number of measurements required at each region and minimise the time taken to acquire an impedance map.

Further features will now be described.

In this regard, the accuracy of the measurement of impedance can be subject to a number of external factors. These can include, for example, the effect of capacitive coupling between the subject and the surrounding environment, the leads and the subject, the electrodes, or the like, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melatonin levels, or the like. A further source of error is the presence of inductive coupling between different electrical conductors within the leads, or between the leads themselves.

Such external factors can lead to inaccuracies in the measurement process and subsequent analysis and accordingly, it is desirable to be able to reduce the impact of external factors on the measurement process.

Figure 13:
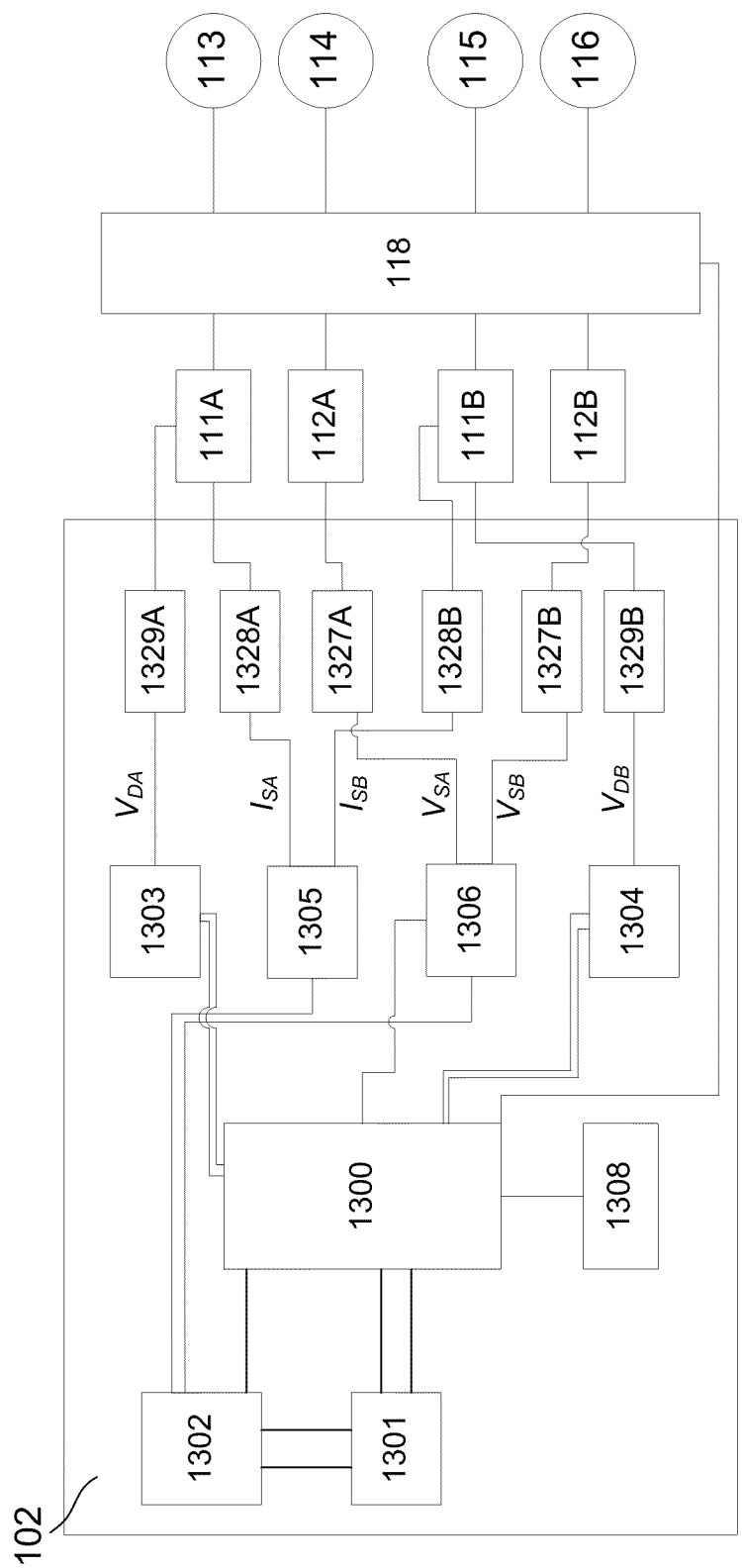
FIG. 13 is a schematic of an example of the functionality of the processing system of FIG. 1A.

A specific example of the functionality implemented by the processing system 102 will now be described with reference to FIG. 13. In this example the processing system 102 implements the functionality using appropriate software control, although any suitable mechanism may be used.

In this example the processing system 102 includes a timing and control module 1300, an interface module 1301, an analysis module 1302, sine wave look up tables (LUTs) 1303, 1304, a current module 1305, and a voltage module 1306.

A number of analogue to digital converters (ADCs) 1327A, 1327B, 1328A, 1328B and digital to analogue converters (DACs) 1329A, 1329B are provided for coupling the processing system 102 to two signal generators 111A, 111B, one of which is provided for each of the drive electrodes, and two sensors 112A, 112B one of which is provided for each of the sense electrodes, as will be described in more detail below.

The signal generators 111A, 111B, and the two sensors 112A, 112B are coupled to the electrodes 113, 114, 115, 116 via the switching device 118, which is in turn connected to the timing and control module 1300. This arrangement allows the timing and control module 1300 to selectively interconnect the signal generators 111A, 111B, the two sensors 112A, 112B and the electrodes 113, 114, 115, 116, allowing different electrode configurations to be provided.

In use, the timing and control module 1300 determines the measurements to be performed, typically in accordance with input commands received from the input 105 via the interface module 1301 and uses this information to access the LUTs 1303, 1304, which in turn cause a digital sine wave signal to be produced based on the specified frequency and amplitude. The digital control signals are transferred to the DAC's 1329A, 1329B, to thereby allow analogue control signals indicative of the voltage drive signals $V_{DA}$, $V_{DB}$ to be produced.

Measured analogue voltage and current signals $V_{SA}$, $V_{SB}$, $I_{SA}$, $I_{SB}$ are digitised by the ADC's 1327, 1328 and provided to the current and voltage modules 1305, 1306. This allows the processing system 102 to determine the current flow by having the current module 1305 determine the total current flow through the subject using the two current signals $I_{SA}$, $I_{SB}$, with an indication of this being provided to the analysis module 1302. The voltage module 1306, which is typically in the form of a differential voltage amplifier, or the like, operates to determine a differential voltage, which is also transferred to the analysis module 1302, allowing the analysis module to determine impedance values using the current and differential voltage signals.

The control module 1300 may also be coupled to a fault detection module 1308. This monitors the magnitude of signals applied to the subject to determine if these are within acceptable threshold levels. If not, the fault detection module 1308 can cause the process to be halted or to allow an alert to be generated.

Figure 14A:
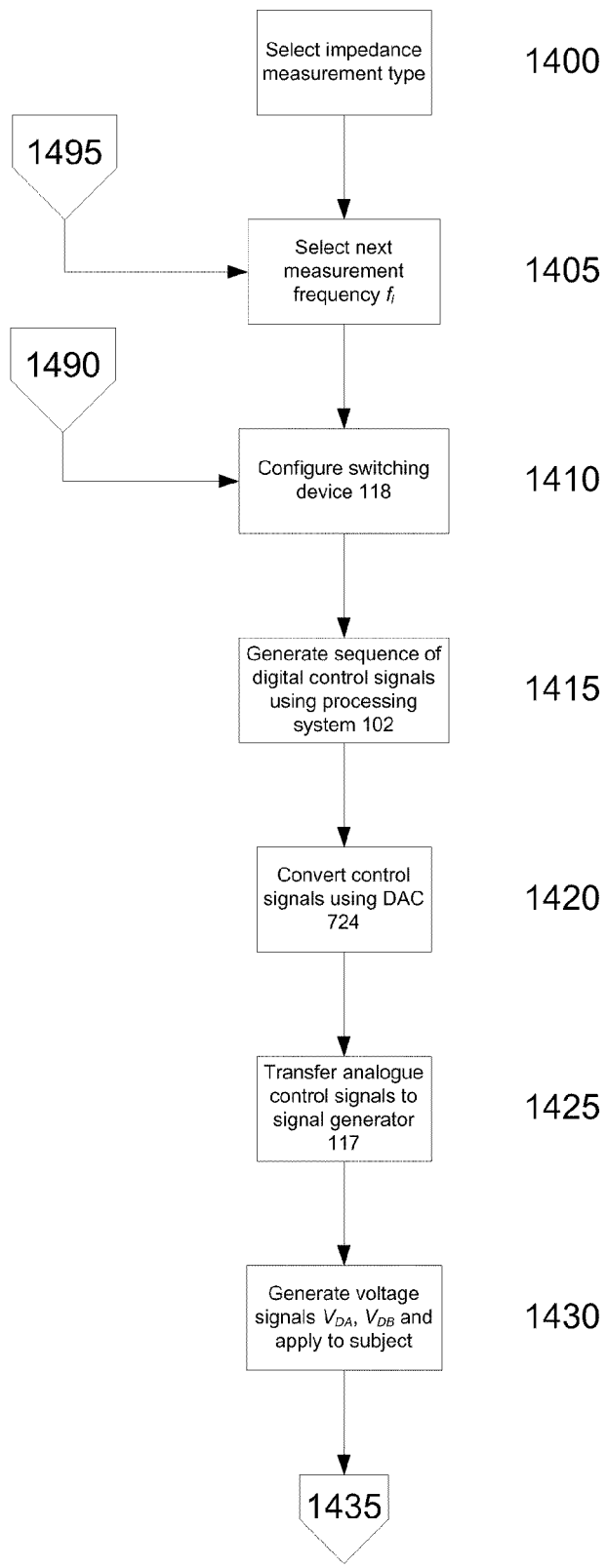
FIGS. 14A to 14C are a flowchart of an example of a process for performing impedance measurements using the apparatus of FIG. 13.
Figure 14B:
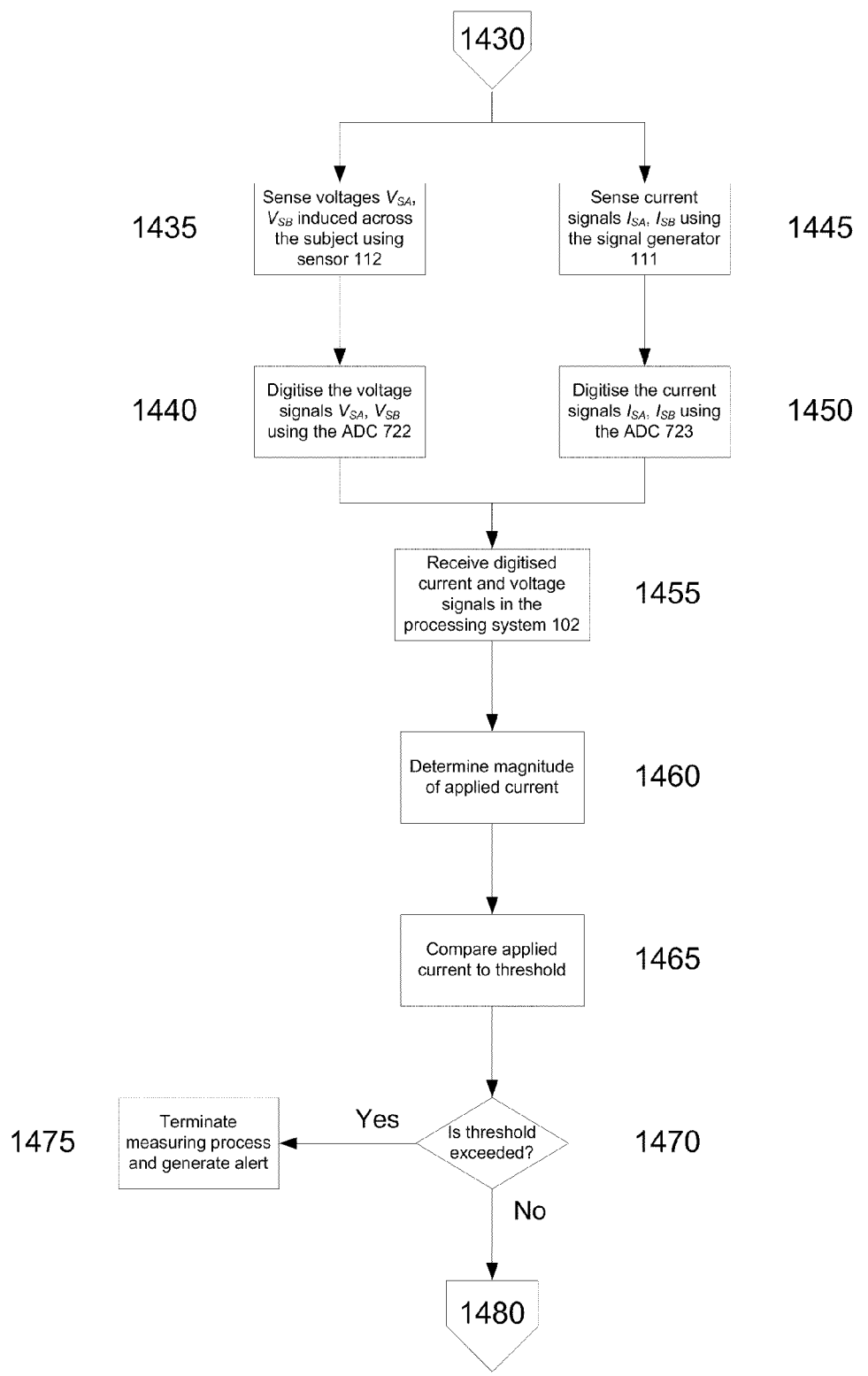
Figure 14C:
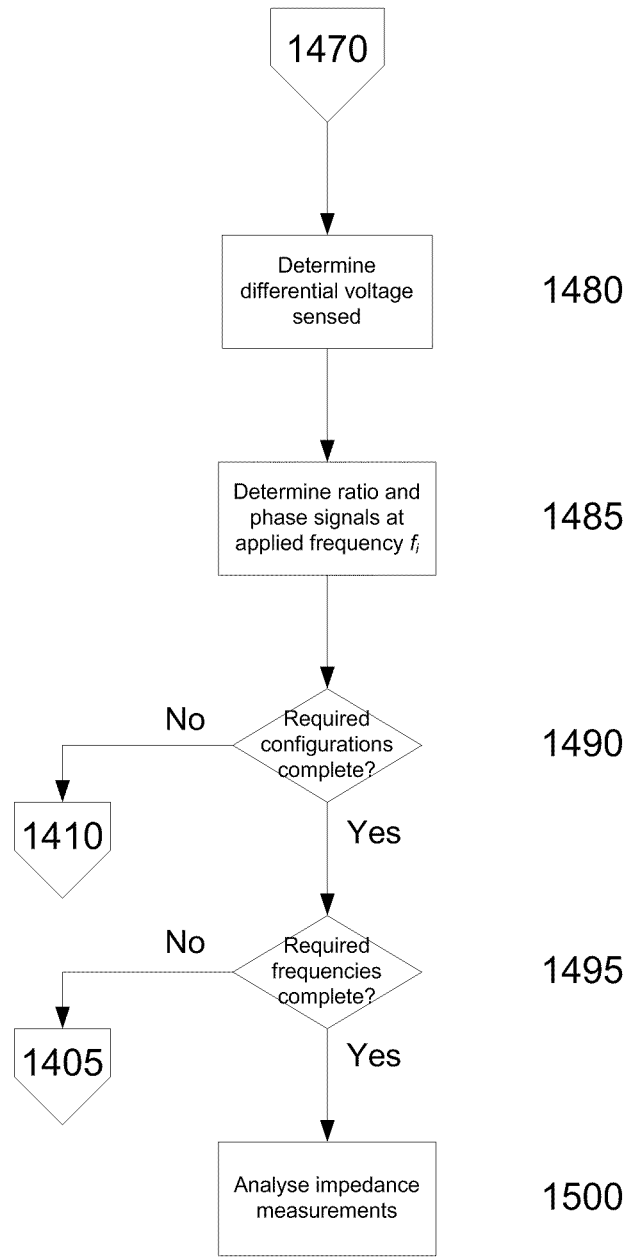

An example of the process for performing impedance measurements for lesion detection, will now be described with reference to FIGS. 14A to 14C.

At step 1400 an impedance measurement type is selected, with the processing system 102 selecting a next measurement frequency $f_i$, at step 1405. Following this, at step 1410, the processing system 102 determines an electrode configuration for a first measurement at a site, and configures the switching device 118 accordingly, so that the signal generators 111A, 111B, and the sensors 112A, 112B are connected to the electrodes 113, 114, 115, 116 as required.

At step 1415, the processing system 102 generates a sequence of digital voltage control signals. The digital control signals are converted to analogue control signals indicative of the voltage drive signals $V_{DA}$, $V_{DB}$ using the DACs 1329A, 1329B at step 1420, allowing the analogue control signals to be provided to each of the signal generators 111A, 111B at step 1425. This causes each signal generator 111A, 111B to generate respective voltage drive signals $V_{DA}$, $V_{DB}$ and apply these to the subject S at step 1430, via the switching device 118 and selected ones of the electrodes 113, 114, 115, 116 acting as drive electrodes.

At step 1435 the voltage induced across the subject is determined by having the sensors 112A, 112B sense voltages $V_{SA}$, $V_{SB}$ at other selected ones of electrodes 113, 114, 115, 116, acting as sense electrodes. Thus, for example, if the electrodes 113, 114 are acting as drive electrodes, the electrodes 115, 116 will act as sense electrodes.

The sensed voltage signals $V_{SA}$, $V_{SB}$ are digitised by the corresponding ADCs 1327A, 1327B at step 1440. At step 1445 current signals $I_{SA}$, $I_{SB}$, caused by application of the voltage drive signals $V_{DA}$, $V_{DB}$, are determined using the signal generators 111A, 111B, with an indication of the current signals $I_{SA}$, $I_{SB}$ being transferred to the ADCs 1328A, 1328B for digitisation at step 1450.

At step 1455 the digitised current and voltage signals $I_{SA}$, $I_{SB}$, $V_{SA}$, $V_{SB}$ are received by the processing system 102 allowing the processing system 102 to determine the magnitude of the applied current $I_S$ at step 1460. This may be performed using the current addition module 1305 in the above described functional example of FIG. 13, allowing the fault detection module 1308 to compare the total current flow $I_S$ through the subject to a threshold at step 1465. If it is determined that the threshold has been exceeded at step 1470 then the process may terminate with an alert being generated at step 1475.

This situation may arise, for example, if the device is functioning incorrectly, or there is a problem with connections of electrodes to the subject, such as if one is not in correct electrical contact with the subject's skin or tissue. Accordingly, the alert can be used to trigger a device operator to check the electrode connections and/or device operation to allow any problems to be overcome. It will be appreciated, that any suitable form of corrective action may be taken such as attempting to restart the measurement process, reconnecting the electrodes to the subject S, reducing the magnitude of the current through the subject, or the like.

At step 1480, the processing system 102 operates to determine the differential voltage sensed across the subject. In the functional example described above with respect to FIG. 13, this can be achieved using the differential voltage module 1306. At step 1485 the analysis module 1302 operates to determine ratio and phase signals, representing the impedance of the subject S, at the applied frequency $f_i$ using the current and differential voltage signals. In the above functional example, this can be performed using the analysis module, and some form of signal analysis, such as phase quadrature analysis, depending on the preferred implementation.

At step 1490, the processing system determines if all required electrode configurations have been analysed. Thus, as described above, it is typical to perform multiple measurements at a given site using a different electrode configuration, and in particular a different combination of drive and sense electrodes. If the required configurations have not been completed, then the process returns to step 1410, allowing the processing system 102 to reconfigure the switching device 118, allowing a different electrode configuration to be implemented.

Thus, for example, if initially the electrodes 113, 114 are acting as drive electrodes, and the electrodes 115, 116 are acting as sense electrodes, then the switching device 118 is reconfigured to provide an alternative configuration, such as having the electrodes 113, 115 act as drive electrodes, and the electrodes 114, 116 act as sense electrodes, allowing the process to be repeated at the different configuration.

If all required configurations have been tried, then at step 1495, it is determined if measurements at each of the frequencies have been performed, and if not, the process may return to step 1405 to allow the process to be repeated at a next measurement frequency $f_i$. It will be appreciated that the use of multiple frequencies may only be required in some circumstances, such as if BIS is being performed, and may not be required in all examples.

Once all required frequencies are complete, at step 1500 the processing system 102 to analyse the impedance measurements, and determine the presence, absence of degree of any anomaly, as described above.

It will be appreciated that in the above example, multiple measurements may be performed at a given site. However, additionally measurements may also be performed over multiple sites, assuming the device 130 has sufficient electrodes to allow this to be performed.

In any event, the above described process this allows a number of impedance measurements to be performed using different electrode configurations, thereby allowing the detection of anomalies, such as lesions, using the techniques outlined above.

Figure 15A:
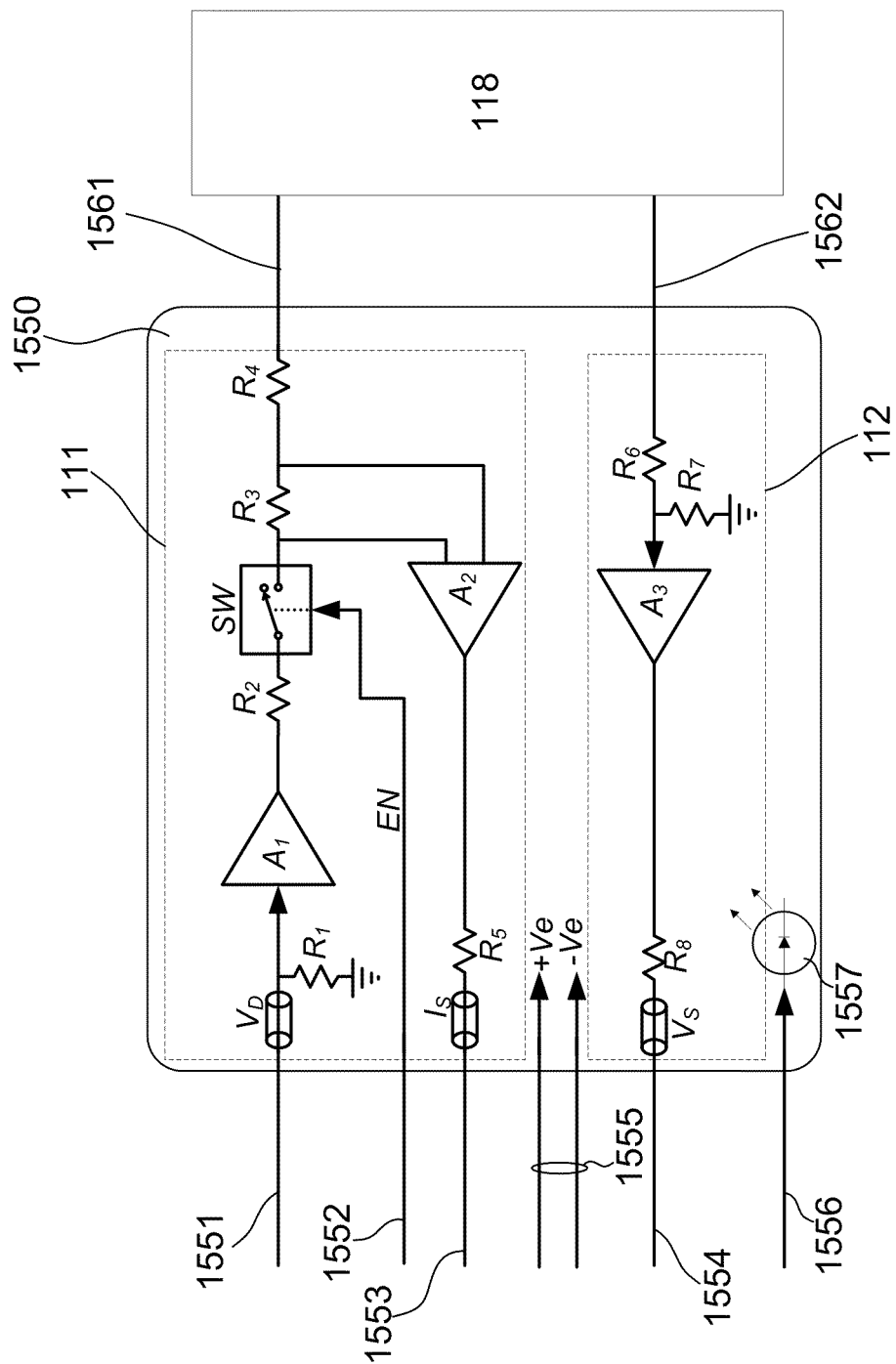
FIG. 15A is a schematic diagram of an example of a sensor and signal generator configuration.

An example of the configuration of the signal generator and sensor for a single one of the channels, will now be described with reference to FIG. 15A.

The apparatus incorporates a substrate 1550, such as a printed circuit board (PCB), or the like, having the respective signal generator 111 and sensor 112 mounted thereon.

The general functionality of the signal generator 111 and sensor 112 are represented by the components shown. In practice a greater number of components may be used in a suitable arrangement, as would be appreciated by persons skilled in the art, and the components shown are merely intended to indicate the functionality of the signal generator and the sensor 111, 112.

The substrate 1550 and associated components may be provided in a suitable housing, such as the handle portion 132 of the probe 130, to protect them during use, as will be appreciated by persons skilled in the art.

The signal generator 111 and the sensor 112 are coupled via respective cables 1561, 1562 to the switching device 118, and it will be appreciated from this that in practice a second signal generator 111 and second sensor 112, having a similar configuration, would also be provided. The switching device, is then coupled to the electrodes 113, 114, 115, as required.

In this example, the signal generator 111 includes an amplifier $A_1$ having an input coupled to a connection 1551. The input is also coupled to a reference voltage, such as ground, via a resistor $R_1$. An output of the amplifier $A_1$ is connected via a resistor $R_2$, to a switch SW, which is typically a CMOS (complementary metal-oxide semiconductor) switch or a relay that is used to enable the voltage source. The switch SW is controlled via enabling signals EN received from the processing system 102 via a connection 1552.

The switch SW is in turn coupled via two resistors $R_3$, $R_4$, arranged in series, and then, via the connection 1561, to the conductive pad 1563. A second amplifier $A_2$ is provided with inputs in parallel with the first of the two series resistor $R_3$ and with an output coupled via a resistor $R_5$, to a connection 1553.

It will be appreciated from the above that the connections 1551, 1552, 1553 therefore forms the lead 123 of FIG. 1A. A range of different resistor values may be used, but in one example, the resistors have values of $R_1=R_2=R_5=50\Omega$, and $R_3=R_4=100\Omega$.

The sensor 111 generally includes an amplifier $A_3$ having an input connected via a resistor $R_6$, to the connection 1562. The input is also coupled via a resistor $R_7$, to a reference voltage such as a ground. An output of the amplifier $A_3$ is coupled to a connection 954, via a resistor $R_7$.

It will be appreciated from the above that the connection 1554 therefore forms the lead 125 of FIG. 1A. A range of different resistor values may be used, but in one example, the resistors have values of $R_6=100\Omega$, $R_7=10M\Omega$ and, $R_8=50\Omega$.

Optional power connections 1555 can be provided for supplying power signals +Ve, −Ve, for powering the signal generator 111 and the sensor 112, although alternatively an on board power source such as a battery, may be used. Additionally, a connection 1556 may be provided to allow an LED 1557 to be provided on the substrate 1550. This can be controlled by the processing system 102, allowing the operating status of the signal generator and sensor to be indicated.

Operation of the signal generator 111 and the sensor 112 will now be described in more detail. For the purpose of this explanation, the voltage drive signal, current signal and sensed voltage will be generally indicated as $V_D$, $I_S$, $V_S$, and in practice, these would be equivalent to respective ones of the voltage drive signals, current signals and sensed voltages $V_{DA}$, $V_{DB}$, $I_{SA}$, $I_{SB}$, $V_{SA}$, $V_{SB}$ in the example above.

In use, the amplifier $A_1$ operates to amplify the analogue voltage signal received from the DAC 1329 and apply this to the subject S via the connection 1561, so that the applied voltage drive signal $V_D$ drives a current signal $I_S$ through the subject S. The voltage drive signal $V_D$, will only be applied if the switch SW is in a closed position and the switch SW can therefore be placed in an open position to isolate the voltage source from the subject S. This may be used if a pair of drive and sense electrodes 113, 115 are being used to sense voltages only, and are not being used to apply a voltage drive signal $V_D$ to the subject S. Isolating the signal generator 111 from the drive electrode 113 removes the unintended return current path(s) that would otherwise be present due to the low output impedance of the amplifier $A_1$, thereby constraining current to flow only between the two selected drive electrodes 113. Other techniques may be used to achieve a similar effect, such as using an amplifier incorporating a high impedance output-disable state.

The current signal $I_S$ being applied to the subject S is detected and amplified using the amplifier $A_2$, with the amplified current signal $I_S$ being returned to the processing system 102, along the connection 1553 and via the ADC 1328.

Similarly, the sensor 112 operates by having the amplifier $A_3$ amplify the voltage detected at the second electrode 115, returning the amplified analogue sensed voltage signal $V_S$ along the connection 1554, to the ADC 1327.

Figure 15B:
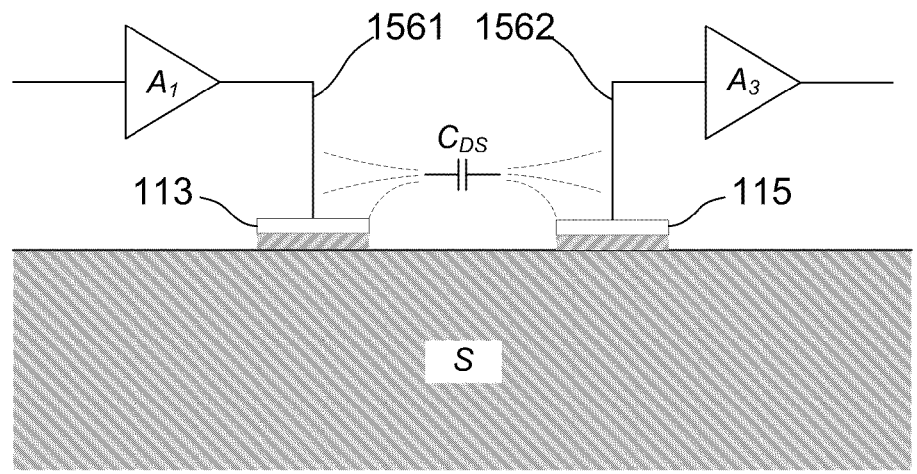
FIG. 15B is a schematic diagram illustrating cross electrode capacitive coupling.

Another potential source of error in impedance measurement processes is caused by cross electrode capacitive coupling. As shown in FIG. 15B, the relative proximity of the electrodes 113, 115 and the corresponding connections 1561, 1562, results in an effective capacitance $C_{DS}$, between the output of the drive amplifier $A_1$ and the input of the sense amplifier $A_3$. Accordingly, this will cause a parasitic current flow between the amplifiers electrodes $A_1$, $A_3$, which can in turn result in inaccuracies in the measurements, particularly at higher frequencies.

Figure 15C:
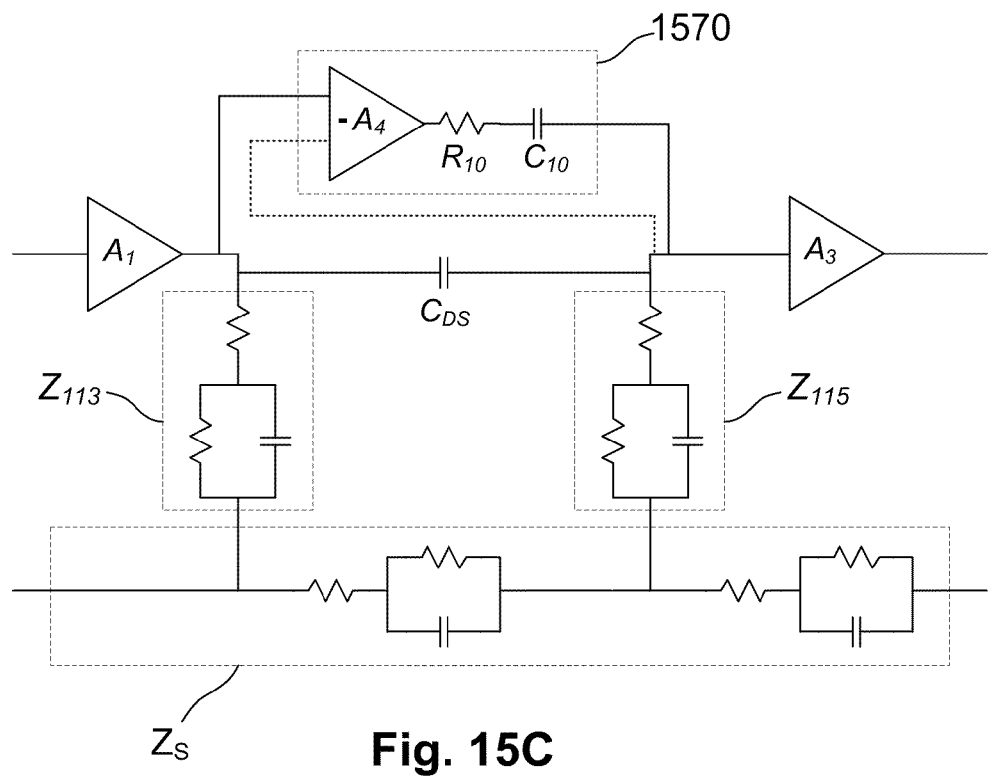
FIG. 15C is a schematic diagram of an example of a cross electrode capacitance canceling circuit; and, FIG. 15D is a schematic diagram of an example of an input capacitance canceling circuit.

To cancel the cross electrode capacitive coupling a cross electrode capacitance cancelling circuit is provided, as shown in FIG. 15C, which shows an equivalent circuit modelling the electrical responsiveness of the electrodes 113, 115 in use.

In this example, the impedances of each electrode 113, 115 and the subject S are represented by respective impedances $Z_{113}$, $Z_{115}$, $Z_S$, formed by respective resistor and capacitor arrangements.

The cross electrode capacitance cancelling circuit 1570 is coupled to the output of the drive amplifier $A_1$ and the input of the sense amplifier $A_3$, and includes an inverting amplifier $A_4$, having an input coupled to the output of the drive amplifier $A_1$ and optionally in a differential arrangement to the input of sense amplifier $A_3$. The output of the inverting amplifier is connected in series via a resistor $R_{10}$ and a capacitor $C_{10}$, to the input of the sense amplifier $A_3$.

In one example, any signal output from the drive amplifier $A_1$ will be inverted and then applied to the input of the sense amplifier $A_3$. By selecting appropriate values for the resistor $R_{10}$ and a capacitor $C_{10}$, this allows the inverted signal to have a magnitude equal to the magnitude of any signal resulting from the effective cross electrode capacitance $C_{DS}$.

In the differential example, the arrangement takes into account the fact that the magnitude of any leakage current between the electrodes is related to the magnitude of the cross electrode capacitance $C_{DS}$ and the voltage across it. Accordingly, the differential arrangement can take this into account by applying a voltage to the capacitor $C_{10}$ which is the same amount above the input of sense amplifier $A_3$ as the output of the drive amplifier $A_1$ is below it.

However, it will be appreciated that the non differential arrangement can be used as this provides a suitable approximation to the differential approach, particularly if appropriate values are selected for the resistor $R_{10}$ and a capacitor $C_{10}$.

In one example, the resistance and/or capacitance of the resistor $R_{10}$ and capacitor $C_{10}$ respectively, can be adjusted, through the use of suitable adjustable components, such as a variable resistor or capacitor. This allows the magnitude and/or phase of the inverted signal to be controlled so that it effectively cancels the signal resulting from the effective cross electrode capacitance $C_{DS}$. It will be appreciated that adjustment of the components may be performed during a calibration process, which will typically include the complete electrode unit together with its associated electrodes attached so that all parasitic capacitances are accurately represented.

Accordingly, the cross electrode capacitance cancelling circuit 1570 provides an effective negative capacitance between the drive electrode 113 and corresponding sense electrode 115, so that a negative current flow occurs, thereby cancelling the parasitic current. This therefore negates the effect of any capacitive coupling between the drive and sense electrodes 113, 115.

Figure 15D:
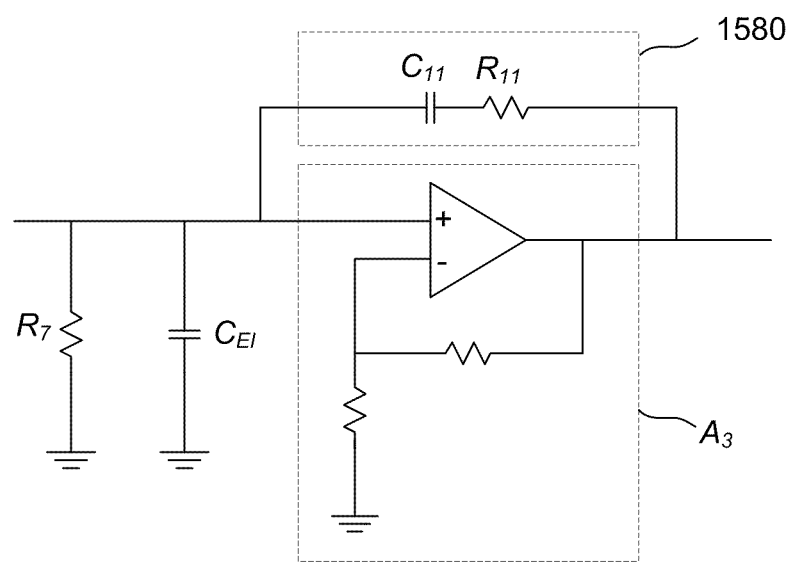

The apparatus may also include an input capacitance cancelling circuit, an example of which is shown in FIG. 15D.

In use, the sense electrodes 115 can capacitively couple to the environment, which results in an effective input capacitance $C_{EI}$ at the input of the sense amplifier $A_3$. The effective capacitance allows signal leakage from the input of the sense amplifier to ground, thereby reducing the signal available at the amplifier input.

Accordingly, in this example, an input capacitance cancelling circuit 1580 is provided which connects the positive amplifier input of the sense amplifier $A_3$ to the output of the sense amplifier, via a resistor $R_{11}$ and a capacitor $C_{11}$. This acts as a positive feedback loop, allowing a proportion of the amplified signal to be returned to the amplifier input. This acts to cancel the reduction in signal at the amplifier input that is caused by the effective input capacitance $C_{EI}$, and therefore provides an effective negative capacitance that cancels the effect of the effective input capacitance $C_{EI}$ at the amplifier input. Again, the input capacitance cancelling circuit requires tuning, which can be achieved during calibration by suitable adjustment of the values of the resistor $R_{11}$ and/or the capacitor $C_{11}$.

As briefly mentioned above, when separate connections 123, 125, are used for the voltage signal $V_S$ and the current signal $I_S$, then inductive coupling between the leads 123, 125 can result in EMFs being induced within the leads 123, 125. The magnitude of the EMF is dependent on the degree of coupling between the leads 123, 125 and hence their physical separation, and also increases in proportion to the frequency and amplitude of the current signal $I_S$. The EMF induced within the leads 123, 125 results in an effective EMF across the input of the sensor 118. As a result, a component of the sensed voltage signal $V_S$ is due to the induced EMF, which in turn leads to inaccuracies in the determined voltage signal $V_S$ and the current signal $I_S$.

The effect of inductive coupling varies depending on the physical separation of the leads 123, 125. Accordingly, in one example, the effect of inductive coupling between leads can be reduced by physically separating the connections 1551, 1552, 1553, 1554, 1555, 1556 as much as possible.

Additionally, as the physical arrangement of connections within the device will be constant any EMF induced along the connections is also substantially constant, allowing this to be accounted for during a calibration process.

Accordingly, when the apparatus 100/130 is initially configured, and in particular, when the algorithms are generated for analysing the voltage and current signals $V_S$, $I_S$, to determine impedance measurements, these can include calibration factors that take into account the induced EMF. In particular, during the configuration process, an apparatus 100/130 can be used to take measurements from reference impedances, with the resulting calculations being used to determine the effect of the induced EMF, allowing this to be subtracted from future measurements.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any subject such as an animal, including but not limited to, primates, livestock, performance animals, such race horses, or the like, as well as to in-vitro samples, or the like.

The above described processes can be used for determining the health status of an individual, including determining the presence, absence or degree of a range of biological anomalies. It will be appreciated from this that whilst the above examples use the term lesion, this is for the purpose of example only and is not intended to be limiting.

Furthermore, whilst the above described examples have focussed on the application of a current signal to allow a voltage to be measured, this is not essential and the process can also be used when applying a voltage signal to allow a current to be sensed.

The above described impedance maps are determined based on the value of the impedance parameter $R_0$. However, it will be appreciated that impedance maps based on other impedance parameters, such as actual measured impedances, or values of $R_\infty$, $Z_c$, or the like.

Whilst the above described techniques have focused on the detection of lesions and other anomalies in the cervix, it will be appreciated that the above described techniques can be used for detecting lesions in a range of situations, and can therefore also be used in the diagnosis of prostate cancer, or the like. The detection of lesions can also be used in cancer screening, as well as in the triage of abnormal cytology or a HPV high risk genotype positive result.

The invention claimed is:

1. An apparatus for use in performing impedance measurements on a subject, the apparatus including:
   a) a probe having a plurality of electrodes, the probe being configured to allow at least some of the electrodes to be in contact with a site defined by cervical tissue of the subject, the probe including:
      i) a probe portion including the plurality of electrodes positioned at an end of the probe portion, the probe portion being shaped to conform to a shape of a vagina and cervix, said probe portion being insertable into the subject to provide for at least a portion of the electrodes to be contactable with cervical tissues; and,
      ii) a handle portion, the probe portion being removably attached to the handle portion allowing the probe portion to be replaced, and the handle portion being configured for allowing the at least some of the electrodes to be positioned in contact with the site; and,
   b) a signal generator for applying drive signals to the subject using drive electrodes;
   c) a sensor for determining measured signals using measurement electrodes;
   d) a switching device for selectively interconnecting the signal generator and the sensor to the electrodes; and,
   e) a processing system configured to allow impedance measurements to be performed using different electrode configurations by selectively interconnecting the signal generator and the sensor to different electrodes using the switching device, the processing system being configured to:
      i) determine at least one first impedance value, measured at a first contacted portion of cervical tissue using a first electrode configuration, the first electrode configuration using a first electrode and a second electrode as drive electrodes and using a third electrode and a fourth electrode as measurement electrodes;
      ii) determine at least one second impedance value, measured at the first contacted portion of cervical tissue using a second electrode configuration, the second electrode configuration using the first electrode and the third electrode as drive electrodes and using the second electrode and the fourth electrode as measurement electrodes;
      iii) determine a difference between the first and second impedance values; and,
      iv) determine an indicator indicative of the presence, absence or degree of an anomaly using the determined difference.

2. An apparatus according to claim 1, wherein the handle portion includes at least one of:
   a) at least part of the processing system;
   b) the signal generator;
   c) the sensor;
   d) the switching device; and,
   e) a capacitance cancelling circuit.

3. An apparatus according to claim 2, wherein the processing system includes a first processing system and a second processing system and wherein at least one of the first and second processing systems is provided in the handle portion.

4. An apparatus according to claim 1, wherein the apparatus includes an electrode array having a number of electrodes provided thereon, and wherein in use, selected ones of the electrodes are used as drive and measurement electrodes.

5. An apparatus according to claim 1, wherein the apparatus includes a capacitance cancelling circuit for cancelling capacitance coupling between first and second electrodes.

6. An apparatus according to claim 5, wherein the capacitance cancelling circuit includes an inverting amplifier for coupling a signal generator output to a sensor input and wherein the inverting amplifier applies a capacitance cancelling signal to the sensor input to thereby cancel any effective capacitance between the first electrode and the second electrode.

7. An apparatus according to claim 6, wherein an inverting amplifier output is coupled to the sensor input via at least one of a resistor and a capacitor, and wherein at least one of the resistor and capacitor are adjustable, thereby allowing a capacitance cancelling signal applied to the sensor input to be controlled.

8. An apparatus according to claim 1, wherein the apparatus includes an input capacitance cancelling circuit for cancelling an effective input capacitance at a sensor input.

9. An apparatus according to claim 8, wherein the apparatus includes a feedback loop for connecting a sensor output to the sensor input, the feedback loop including at least one of a resistor and a capacitor, wherein at least one of the resistor and capacitor are adjustable, thereby allowing a current flow from the sensor output to the sensor input to be controlled, and wherein the feedback loop applies an input capacitance cancelling signal to the sensor input to thereby cancel any effective capacitance at the sensor input.

10. An apparatus according to claim 1, wherein the processing system determines an impedance value for each of at least four electrode configurations.

11. An apparatus according to claim 1, wherein the processing system is configured to:
   a) cause at least one drive signals to be applied to the subject;
   b) measure at least one induced signal across the subject; and,
   c) determine at least one impedance value using an indication of the drive signal and the induced signal.

12. An apparatus according to claim 1, wherein the processing system is configured to:
   a) determine impedance values at a number of different sites; and,
   b) determine an impedance map using the impedance values at each site.

13. An apparatus according to claim 12, wherein the processing system is configured to:
   a) determine the presence of an anomaly at any one of the sites; and,
   b) determine the impedance map taking the anomaly into account by at least one of:
      i) excluding the site from the impedance map; and,
      ii) modifying the impedance value determined for the site.

14. An apparatus according to claim 1, wherein the processing system is configured to:
   a) compare the difference to a reference; and,
   b) determine an anomaly depending on the result of the comparison.

15. An apparatus according to claim 14, wherein the reference is a previously measured difference for the subject.

16. An apparatus according to claim 1, wherein the impedance values are at least one of:
   a) measured impedance values; and,
   b) impedance parameter values derived from measured impedance values, wherein the impedance parameter values include at least one of:
      i) an impedance at infinite applied frequency ($R_\infty$);
      ii) an impedance at zero applied frequency ($R_0$); and,
      iii) an impedance at a characteristic frequency ($Z_c$).

17. An apparatus according to claim 1, wherein the processing system is configured to:
   a) cause at least one first impedance value to be measured at the first contacted portion of cervical tissue using a first electrode configuration; and,
   b) cause at least one second impedance value to be measured at the first contacted portion of cervical tissue using a second electrode configuration.

18. An apparatus according to claim 1, wherein the anomaly includes any one or a combination of:
   a) a tissue anomaly; and,
   b) an erroneous measurement.

* * * * *